US009495759B2

(12) United States Patent
DeMartin et al.

(10) Patent No.: US 9,495,759 B2
(45) Date of Patent: Nov. 15, 2016

(54) MOBILE, WEARABLE, AUTOMATED TARGET TRACKING SYSTEM

(71) Applicant: APEIROS, LLC, San Clemente, CA (US)

(72) Inventors: Frank DeMartin, San Clemente, CA (US); Erik Walton, Corona, CA (US); Ricardo Peregrino, Port Townsend, WA (US)

(73) Assignee: APEIROS, LLC, San Clemente, CA (US)

( * ) Notice: Subject to any disclaimer, the term of this patent is extended or adjusted under 35 U.S.C. 154(b) by 0 days.

(21) Appl. No.: 14/633,083

(22) Filed: Feb. 26, 2015

(65) Prior Publication Data
US 2016/0189391 A1    Jun. 30, 2016

Related U.S. Application Data
(60) Provisional application No. 61/944,994, filed on Feb. 26, 2014.

(51) Int. Cl.
| | | |
|---|---|---|
| *G06T 7/00* | (2006.01) | |
| *G06T 7/20* | (2006.01) | |
| *H04N 5/77* | (2006.01) | |

(Continued)

(52) U.S. Cl.
CPC ............... *G06T 7/20* (2013.01); *G01B 11/026* (2013.01); *G06F 1/163* (2013.01); *G06F 3/012* (2013.01); *G06K 9/00711* (2013.01); *G06K 9/00771* (2013.01); *G06T 7/004* (2013.01); *G08B 13/19602* (2013.01); *G08B 13/19608* (2013.01); *H04N 5/77* (2013.01); *A61B 2034/2057* (2016.02); *G06K 2209/21* (2013.01); *G06T 2207/30241* (2013.01)

(58) Field of Classification Search
CPC ....... G06T 7/20; G06T 7/004; G06T 7/2093; G06T 2207/30241; G06K 9/00711; G06K 9/00718; G06K 9/00724; G06K 9/00771; G06K 2209/21; G06K 2209/40; G06F 1/163; G06F 3/012; A61B 2034/2057; G08B 13/19602; G08B 13/19608; G08B 13/19621; G08B 13/1963; G08B 13/1966; G01B 11/026
See application file for complete search history.

(56) References Cited

U.S. PATENT DOCUMENTS 5,155,491 A * 10/1992 Ando ...................... G01S 19/28
                                                        342/357.67
5,375,059 A * 12/1994 Kyrtsos .............. B60K 31/0008
                                                        342/357.24

(Continued)

*Primary Examiner* — Manav Seth
(74) *Attorney, Agent, or Firm* — One LLP

(57) ABSTRACT

The mobile, wearable, automated target tracking system is designed to enable an image and/or sound recording device, such as a video camera or directional microphone, to automatically follow a subject (or target) in order to keep that subject within the image frame or sound range that is being recorded. The automated target tracking system makes it possible to capture both the action and subject simultaneously without requiring a cameraman to manually operate the equipment. The indoor/outdoor, automated tracking system is designed to be independent of the video/sound recording device and may utilize a smartphone for location sensing and control. Both the target (or subject) and the tracking device may be moving, so the tracking device is designed to adjust position on 3 axes, azimuth (pan), elevation (tilt) and horizon (roll). Since the compact, battery-operated tracking device is mobile and wearable, it enables the user to capture the subject and all the action while also participating in the activity at the same time.

17 Claims, 15 Drawing Sheets

(51) Int. Cl.
*G06K 9/00* (2006.01)
*G06F 3/01* (2006.01)
*G06F 1/16* (2006.01)
*G08B 13/196* (2006.01)
*G01B 11/02* (2006.01)

(56) References Cited

U.S. PATENT DOCUMENTS

| | | | | |
|---|---|---|---|---|
| 7,447,331 B2 * | 11/2008 | Brown | ............. | G08B 13/19604 348/169 |
| 7,936,385 B2 * | 5/2011 | Konno | ................. | G01S 3/7864 348/169 |
| 8,212,877 B2 * | 7/2012 | Ono | ................. | G08B 13/19608 348/162 |
| 8,323,106 B2 * | 12/2012 | Zalewski | ............. | G06F 3/0304 30/32 |
| 8,465,376 B2 * | 6/2013 | Bentley | ............. | A63B 24/0006 473/219 |
| 8,540,560 B2 * | 9/2013 | Crowley | ............ | A63B 24/0062 273/317 |
| 8,579,632 B2 * | 11/2013 | Crowley | ................ | G06Q 30/02 434/247 |
| 8,693,726 B2 * | 4/2014 | Karakotsios | ....... | G06K 9/00355 348/169 |
| 8,731,239 B2 * | 5/2014 | Gefen | .................. | G01S 3/7864 348/143 |
| 8,827,824 B2 * | 9/2014 | Bentley | .................. | A63B 69/36 473/199 |
| 8,903,521 B2 * | 12/2014 | Goree | ................ | A61B 5/1118 700/90 |
| 9,230,300 B2 * | 1/2016 | Bekaert | ................ | G06T 3/4038 |
| 9,237,885 B2 * | 1/2016 | Stein | ...................... | A61B 17/00 |
| 9,255,813 B2 * | 2/2016 | Liu | ......................... | G06F 3/011 |
| 9,258,982 B1 * | 2/2016 | Golden | ................ | A01K 11/008 |
| 9,274,597 B1 * | 3/2016 | Karakotsios | ............ | G06F 3/012 |
| 2008/0300055 A1 * | 12/2008 | Lutnick | ............... | G07F 17/3209 463/39 |
| 2010/0199232 A1 * | 8/2010 | Mistry | .................... | G06F 1/163 715/863 |
| 2010/0204616 A1 * | 8/2010 | Shears | ................ | A61B 5/1127 600/595 |
| 2012/0302349 A1 * | 11/2012 | Marks | ..................... | G06F 3/017 463/38 |
| 2013/0063432 A1 * | 3/2013 | Kaps | ....................... | G06T 13/40 345/419 |
| 2014/0168100 A1 * | 6/2014 | Argiro | ................. | G06F 3/0416 345/173 |
| 2014/0320629 A1 * | 10/2014 | Chizeck | ................ | G06F 3/016 348/81 |

\* cited by examiner

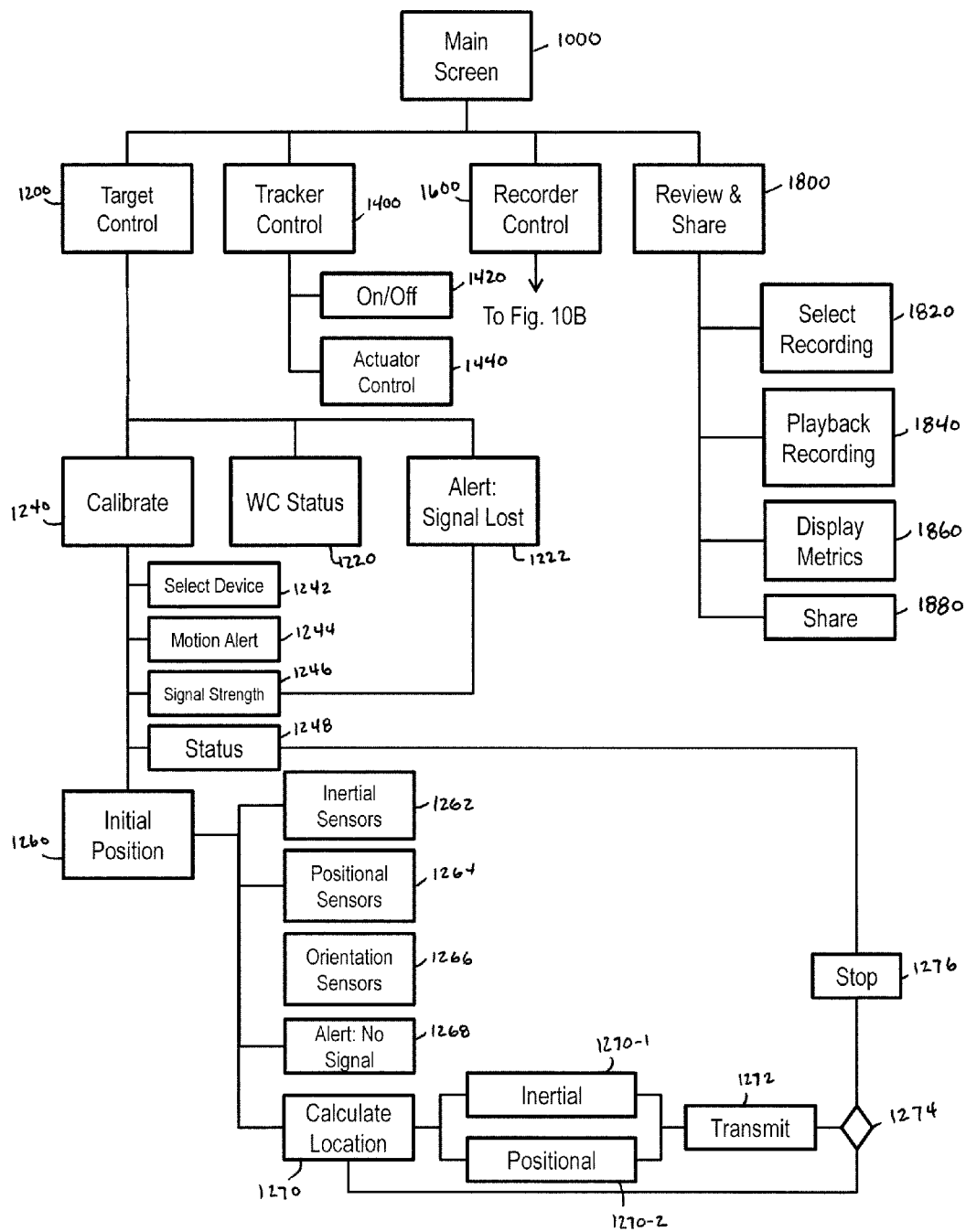

MOBILE, WEARABLE, AUTOMATED TARGET TRACKING SYSTEM

CROSS REFERENCE TO RELATED APPLICATIONS

This application is related to U.S. Provisional Application No. 61/944,934, filed on Feb. 26, 2014, the entire contents and disclosure of which is herein incorporated by reference.

BACKGROUND OF THE INVENTION

The present invention relates to the field of automated target tracking and recording systems.

Video and still cameras have until recently been primarily used to capture images of a subject, person(s) or scenery, in order to be shared with others or be viewed at a later time. However, with the introduction and mass adoption of the wearable point-of-view (POV) camera, the subject is no longer a person(s), but rather the user's point of view. Or more simply the camera's subject is now what the user is seeing or experiencing. And when the POV camera user is jumping off a cliff or extreme skiing in the Rockies, the user's experience, or the subject of the POV video, can be very exciting indeed. This new camera use case has created an expanding market for wearable cameras and accessories.

Although capturing a user's POV during extreme action sports can produce fantastic video footage, the story is not complete without the actor or actors involved.

It is therefore desirable to provide improved automated target tracking and recording systems that address the shortcomings described above.

BRIEF DESCRIPTION OF THE DRAWINGS

Illustrated in the accompanying drawing(s) is at least one of the best mode embodiments of the present invention.

FIG. 10A-B illustrates an exemplary user interface flow chart in accordance with at least one embodiment of the present invention.

DETAILED DESCRIPTION OF THE PREFERRED EMBODIMENTS

Figure 1:
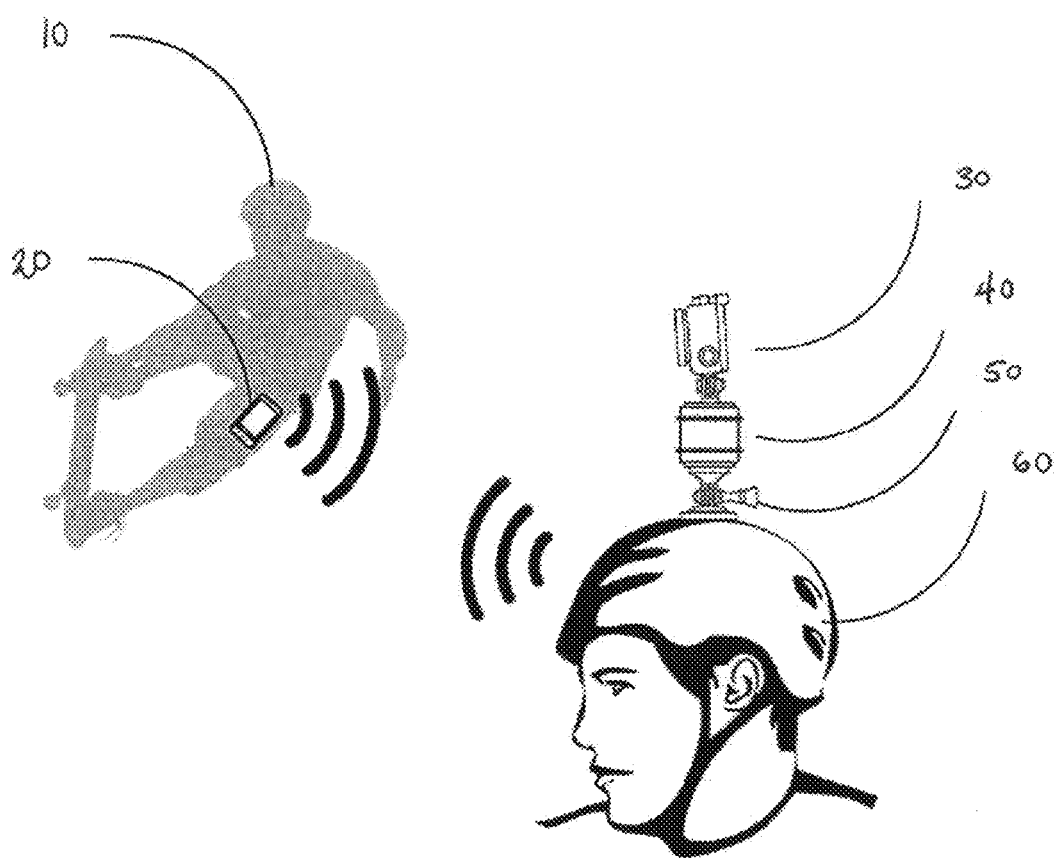
FIG. 1-1A schematically illustrates a recording system according to at least one embodiment of the present invention.

The above-described drawing figures illustrate the described invention in at least one of its preferred, best mode embodiment, which is further defined in detail in the following description. Those having ordinary skill in the art may be able to make alterations and modifications to what is described herein without departing from its spirit and scope. While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment(s) illustrated. Therefore, it should be understood that what is illustrated is set forth only for the purposes of example and should not be taken as a limitation on the scope of the present invention.

FIG. 1 schematically illustrates a recording system according to at least one embodiment of the present invention.

The recording system generally includes a target device 20 associated with a subject 10, a recording device 30 for recording the subject, a tracking device 40 cooperatively coupled to the recording device for positioning the recording device to record the subject in response to movement of the target device, and a mounting device 50 for mounting the tracking device and the recording device to a mounting location 60.

In general, the recording system may be utilized where it is desirous to record the subject while the subject is in motion. For example, the subject may be performing some athletic or sports related activity, such as skiing, biking, surfing, snowboarding, skateboarding, etc., for which the subject's movement may be largely unpredictable, inconsistent, or otherwise generally irregular. The target device is preferably carried on the subject's person and is tracked via the tracking device, which repositions the recording device accordingly such that the subject remains within a recording range of the recording device (i.e., within the ability of the recording device to satisfactorily record the subject) for an extended period of time despite the subject's movement. In this manner, the recording system maintains the subject within the recording range for longer than if the recording device were not repositioned according to the subject's movement.

Additionally, the mounting location may be either stationary or non-stationary depending on the desired recording. For example, the mounting device may be operable to secure the tracking device and recording device to headgear worn by a recording user who may follow, pace or otherwise move relative to the subject. In this manner, the subject may further be maintained within the recording range for an extended period of time despite the subject's movement. As an additional example, the mounting device may be operable to secure the tracking device to a stationary tripod.

Figure 1A:
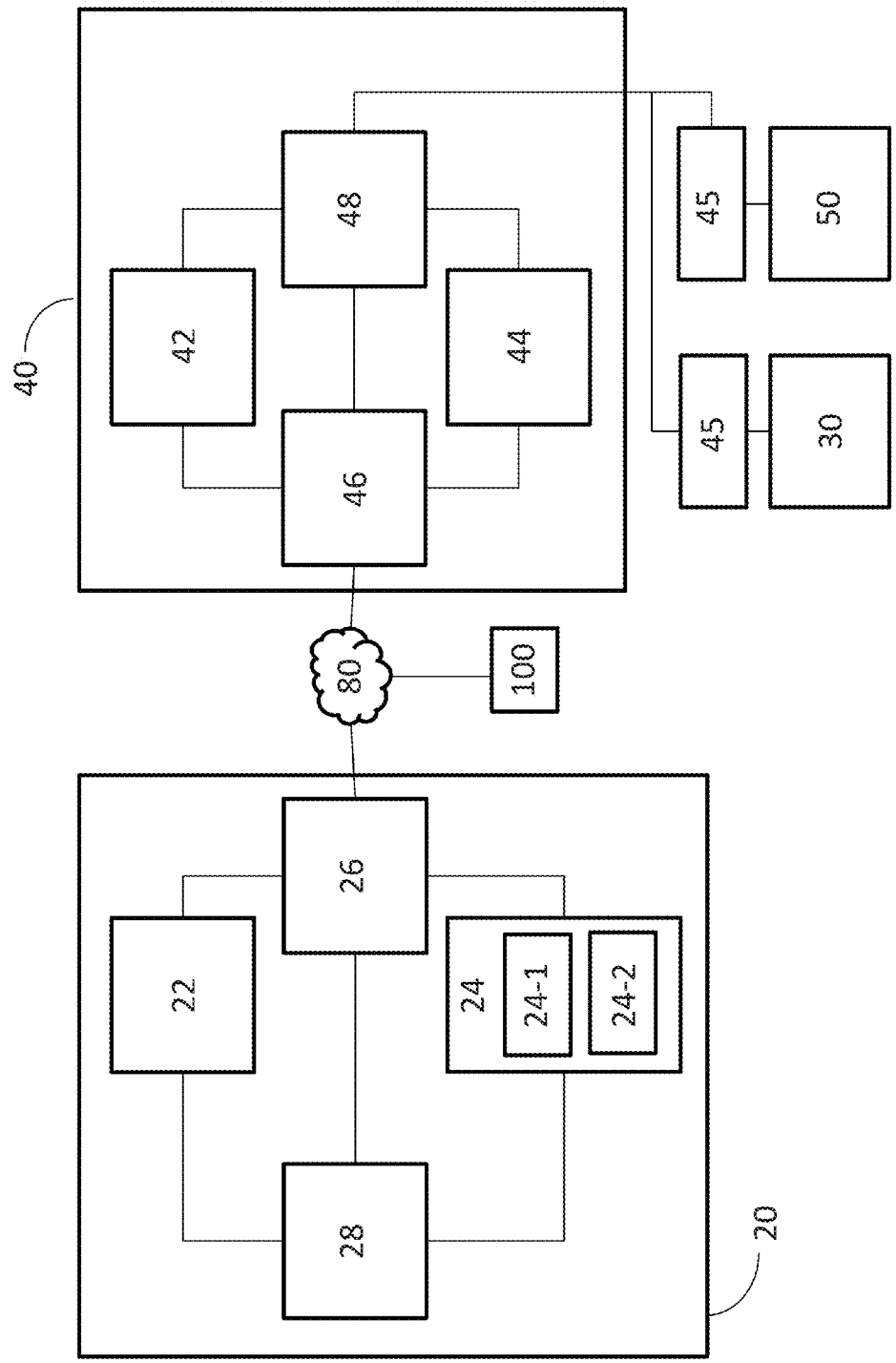

As shown for example, in FIG. 1A, the target device comprises a motion sensor 22 (e.g., one or more accelerometers, gyroscopes, compasses, barometers, etc.) for sensing the motion of the target device and generating motion data therefrom, a position signal generator 24 for generating a position signal; a wireless transceiver 26 communicatively coupled to the motion sensor and position beacon for transmitting the motion data and the position signal over a wireless network 80 (e.g., RF, Bluetooth, cellular, PAN, satellite, etc.) to the tracking device; and a controller 28 for controlling the operation of the target device according to the functionalities set forth herein. An internal battery (not shown) may further be provided to power the electrical components of the target device.

As shown for example, in FIG. 1A, the tracking device comprises a tracking motion sensor 42 (e.g., one or more accelerometers, gyroscopes, compasses, barometers, satnav receivers, etc.) for sensing the motion of the tracking device (including the position thereof and the non-motion of the tracking device) and generating motion data therefrom; a recording device orientation sensor 44 for sensing the orientation of the recording device and generating recording range data therefrom; and a wireless transceiver 46 for receiving the motion data and position signal transmitted by the target device; and a controller 48 for controlling the operation of the tracking device according to the functionalities set forth herein. An internal battery (not shown) may further be provided to power the electrical components of the tracking device.

Communicatively coupled to the tracking device is the recording device, as reflected in FIGS. 1, 9, 11, 14, and 15, for example, which may be any type of recording device, and is preferably capable of recording at least one of: images, sound, biometrics, kinetics, or other types of data capable of being recorded. Recordings may be retrievably stored in a memory (located in one of the devices, or at connected server system) so as to be later accessed by users. Motion data, recording range data (e.g., recording device orientation data) and/or any other type of data utilized by the system may also be retrievably stored in the memory in association with the recording to be later accessed by users. It will be appreciated that as used herein, the term 'recording range' refers the ability of the recording device to satisfactorily record the subject. For example, a still camera's recording range would include the frame of its view and where it is focused. It will further be appreciated that the recording range, as used herein, is not necessarily a static range and may be mechanically and/or electrically altered. Keeping with the still camera example, the recording range of the still camera may be altered by reorienting and/or refocusing the camera onto a different view.

In some embodiments, the position signal generator comprises a position beacon 24-1 for generating the position signal including beacon position data. When the position signal is received by the tracking device, the beacon position data utilized to calculate the relative position of the target with respect to the tracking device and/or recording device.

In some embodiments, the position signal generator comprises a geo-spatial position signal generator 24-2 for receiving geo-spatial position data from a geo-spatial positioning system 100 (e.g., GNSS, GPS, GLONASS, BeiDou, QZSS, etc.) and generating the position signal therefrom, including geo-positional data indicating the geo-positional location of the target. When the position signal is received by the tracking device, the geo-positional data utilized to calculate the relative position of the target with respect to the tracking device and/or recording device.

It will be appreciated that the position data may comprise both beacon data and geo-positional data, generated in accordance with the functionalities described herein.

As shown, for example, in FIG. 1A, the tracking device is operatively coupled to one or more of: the recording device and the mount via one or more actuators 45 for changing the relative orientation of one or more of: the recording device with respect to the tracking device, and the tracking device with respect to the mount. The recording device orientation sensor may further sense one or more of: the orientation of the recording device relative to the tracking device, the orientation of the tracking device relative to the target, the orientation of the tracking device relative to the recording device; and generate orientation data therefrom. The orientation data may be utilized to calculate the orientation of the recording device relative to the target device, and thereby generate the recording range data therefrom. In some embodiments, the actuators operate to change one or more of: the azimuth (i.e., pan), the elevation (i.e., tilt), horizon (i.e., roll), the distance (i.e., zoom), the focus, and activation (i.e. on/off) of the recording device by mechanical and/or electrical means.

Returning to FIG. 1, in some embodiments, the tracking device is operatively coupled to the recording device in the form of a camera 30, which is communicatively coupled via the wireless network to the target device in the form of a smart phone 20 operating a software application whose execution imparts the smart phone with the functionalities of the target device described herein.

In operation, the target device periodically (i.e., continuously or at regular or irregular intervals) transmits its motion data and the position signal (including beacon and/or geo-spatial position data) to the tracking device. The tracking device utilizes the position signal and motion data transmitted by the target device and received by the tracking device as well as the target device motion data and recording range data to calculate the position and trajectory vectors of the target device relative to the tracking device—or more particularly, relative to the recording range of the recording device coupled to the tracking device, of which the position and trajectory vectors relative to the tracking device may (in some embodiments) be a proxy for. The tracking device utilizes the calculated position and trajectory vectors to adjust the recording range of the recording device, via for example the actuators, such that the target device—or more particularly, the subject carrying the target device—is within (or remains within) the recording range of the recording device while the recording device is recording. The recording range may be adjusted by changing the azimuth (i.e., pan), the elevation (i.e., tilt), horizon (i.e., roll), the distance (i.e., zoom), the focus, and/or activation (i.e. on/off) of the recording device by mechanical and/or electrical means. In other words, the tracking device anticipates where the target device is going to be, and where the recording range is going to be (based on trajectory and orientation), and then adjusts the recording range to coincide with where the target device is going to be.

One or more feedback loops may further be employed to continuously and in real-time adjust the recording range based the aforementioned calculations. In this manner, the recording device can satisfactorily record the subject in action. Such recordings may be still-frame or live-action video recordings, or other types of recordings, including metric data recordings (e.g., speed, position, acceleration, weight, etc.).

Figure 2A:
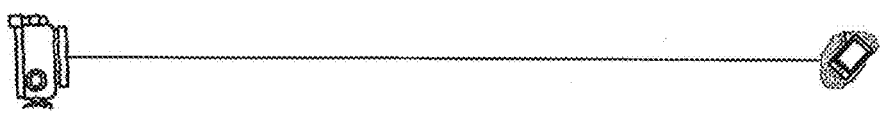
FIG. 2A schematically illustrates an initial relative position of the target device and the tracking device $P_1$ at an initial time $T_1$.
Figure 2B:
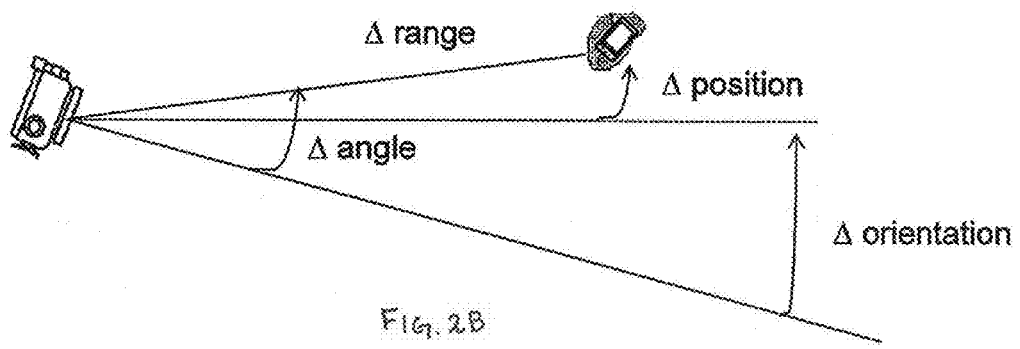
FIG. 2B schematically illustrates a later relative position of the target device and the tracking device $P_2$ at some later time $T_2$.

An exemplary tracking process will now be described with particular attention to FIGS. 2A-2B. FIG. 2A schematically reflects an initial relative position of the target device and the tracking device $P_1$ at an initial time $T_1$. FIG. 2B schematically reflects a later relative position of the target device and the tracking device $P_2$ at some later time $T_2$.

At the initial time $T_1$, the target device transmits its motion data and/or position data to the tracking device from which the tracking device calculates its relative position $P_1$ and alters the orientation of the recording device so as to place the subject within the recording range. At the some later time $T_2$, the target device transmits its motion data and/or position data to the tracking device from which the tracking device calculates its relative position $P_1$ as well as its trajectory vectors (i.e., the anticipated path of the target device/subject), and alters the orientation of the recording device so as to maintain the subject within the recording range. Preferably, because—at least in some scenarios—the target device and/or the tracking device may be moving quickly and/or erratically, the tracking process is capable of tracking such movement. Accordingly, direct transmission of the relevant data via radio-frequency ("RF") signal, or other quickly transmitted signal, is preferred over indirect transmissions, or other more slowly transmitted signal. However, in at least some embodiments, a one or more alternative signal types are utilized as checks on a primary signal type. In at least some embodiments, the tracking process described herein includes interpolating the target device position between times $T_1$ and $T_2$.

One of skill in the art will appreciate that if the relative position of the target device at the later time is unchanged—or the change is small enough that the subject is unlikely to be outside the recording range—then the tracking device need not adjust the orientation of the recording device. One of skill in the art will also appreciate that the embodiments described herein are applicable to situations in which there is an anticipated window of time where the target device/subject is within the outer-bounds of possible recording ranges. For example, when video recording a downhill skier from a stationary mid-run mounting location, the outer limits of how far the recording range can be adjusted may not enable satisfactorily recording of the skier at the top and bottom of the run. In such instances (and those similar to it), it may be desirable to orient the recording device to at or near where the target device/subject is anticipated to enter the outer limit of the adjustable recording range. In the downhill skier example, this would mean that the skier is tracked as he/she progresses from the top of the run, and video recorder is pointed and focused to (or near to) the anticipated mid-run spot where the skier will enter the outer limit of the adjustable recording range. The target device/subject may then be tracked—and consequently recorded—along its anticipated trajectory to at or near where the target device/subject is anticipated to exit the outer limit of the adjustable recording range. In the downhill skier example, this would mean the skier is tracked and recorded through to the mid-run point where satisfactory recording is no longer feasible. In this manner, the recording system may prolong the duration in which the target device/subject is recorded in action.

It should be further noted that in at least some embodiments, the outer bounds of possible recording ranges may be preset according to user preferences and/or mechanical limits. For example, if video recording the end of a skiing run is undesirable, the outer bounds of the possible video recording range may be set to exclude the end of the skiing run. Thus, the end of the skiing run will not be tracked.

In some embodiments, a purely inertial navigation process ("INS") is employed, whereby the initial relative position $P_1$ provides a reference point to which the target device's sensed acceleration and velocity vectors (i.e., trajectory vectors) may be applied to calculate the target device's anticipated trajectory as a function of time. The reference point may be provided during, for example, an initial calibration of the tracking device and target device. Notably, the trajectory vectors of acceleration and velocity are provided here for illustrative purposes; other trajectory vectors than acceleration and velocity may be sensed and applied to calculate the anticipated trajectory without departing from the scope of the embodiments described herein.

In some embodiments, a purely geo-positional navigational process is employed, whereby the relative initial position $P_1$ provides a reference point with which the target device's sensed relative later position $P_2$ may be employed to calculate the anticipated trajectory of the target device as a function of time. The reference point may be provided during, for example, an initial calibration of the tracking device and target device. Moreover, in some embodiments, the relative positions $P_1$ and $P_2$ may be calculated via triangulation from some independent reference point (e.g., a stationary tripod, a GNSS system, etc.).

Preferably, a combined inertial and geo-positional navigational process is utilized to minimize and correct for drift (or other errors) that may be otherwise experienced. A feedback loop may further be employed to adjust the calculated anticipated trajectory based on the actual trajectory sensed, so as to further correct for drift or other errors. It should be noted that other INS and/or geo-positional navigation systems ("GNSS") now known or later developed may be utilized without departing from the scope of the invention.

In operation, the target device is operable to be tracked at close range (i.e., well within the recording range) as well as at far range (i.e., well without the recording range). In most circumstances, it is preferable for the target device to be communicatively coupled directly via an RF-signal—particularly an RF-signal utilizing the unlicensed radio frequency spectrum. In some embodiments, the target and tracking devices are communicatively coupled via a wireless Internet connection. In some embodiments, cellular, near-me area ("NAN"), local-area ("LAN"), metropolitan-area ("MAN"), and/or wide-area ("WAN") networks may be utilized. It should be understood in any event however that the wireless communication range between the target and tracking devices may be variable depending on the transceiver gain of the respective devices and/or the surrounding terrain.

Figure 3:
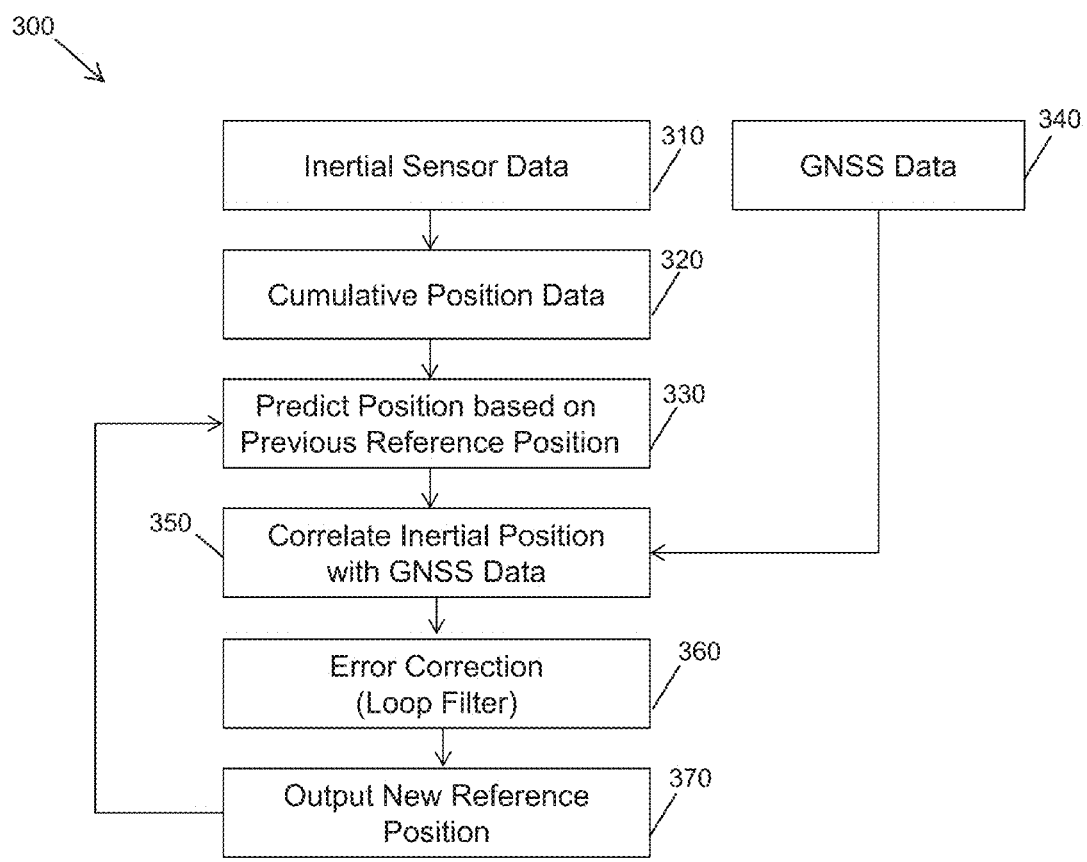
FIG. 3 schematically illustrates an exemplary process for employing a feedback loop and augmented error correction according to at least one embodiment of the present invention.

FIG. 3 illustrates an exemplary process 300 for employing a feedback loop and augmented error correction according to at least one embodiment of the present invention. In this context, augmented error correction refers to the correction of errors in position locating as accomplished via the direct sensors of the tracking device/target device by utilizing external geo-position location techniques, such as those of GNSS, and associated satellite based augmentation systems ("SBAS"), ground based augmentation systems ("GBAS"), wide area augmentation systems ("WAAS"), local area augmentation system ("LASS"), European geostationary navigation overlay service ("EGNOS"), GPS aided geo-augmented navigation ("GAGAN"), multi-functional satellite augmentation system ("MSAS"), and other similar techniques. For illustrative purposes, augmentation utilizing GNSS data will be described with reference to FIG. 3.

At Step 310, inertial sensor data is provided by the target and/or tracking devices. The inertial sensor data is motion data and/or position data generated by the respective target and/or tracking device sensors, as described herein. The inertial sensor data also preferably includes instant inertial sensor data as well as past inertial sensor data. In other words, the history of the sensed relative movement of the target device is provided.

At Step 320, the inertial sensor data is utilized to calculate cumulative position data according to the functionalities described herein. Cumulative position data is data reflecting the past trajectory of the target device, as well as the target device's current position and trajectory vectors. In other words, at Step 320, the target device's current and past motion states in three-dimensional vector space is calculated.

At Step 330, the cumulative position data is utilized to predict an anticipated trajectory, i.e., where the target device will be at some later time. This calculation is based at least partially on the past trajectory of the target device, the current position of the target device, and the trajectory vectors as sensed and calculated according to the functionalities described herein. In other words, at Step 330, where the target device will be is calculated based on where it was, where it is, how it got there, and what it is currently doing.

At Step 340, GNSS data is provided that indicates the absolute positions of the target device and the tracking device. The GNSS data may be provided periodically at regular or irregular intervals, but is preferably provided at a rate that is less frequent than the rate the inertial sensor data is provided.

At Step 350, the inertial sensor data is correlated with the GNSS data and an error function is calculated. The inertial sensor data is typically provided quicker, but is more prone to error; the GNNS data is typically more stable, but is provided slower. Thus, the GNSS data is utilized to calculate any errors in the accuracy of motion data sensed by the respective sensors of the tracking and target devices at a common time between the motion data and the GNSS data. In other words, the GNSS data is utilized to determine how far off the GNSS sensed trajectory the device sensed trajectory is. As the GNSS data is typically less frequent than the inertial sensor data, the error is preferably calculated as a dynamic error function derived from errors at a plurality of common time data points.

At Step 360, the error function is applied to the inertial sensor data to generate augmented inertial sensor data. In other words, the error function is utilized to augment the 'where it was, where it is, and how it got there' described above.

At Step 370, the augmented inertial sensor data is reintroduced in a feedback loop to the process at Step 310 to replace the un-augmented inertial sensor data, and the anticipated trajectory is calculated according to the augmented inertial sensor data and any newly introduced as-of-yet un-augmented inertial sensor data. In other words, the augmentation makes the past position data points more accurate, which in turn makes the 'where it was, where it is, and how it got there' described above more accurate, which it turn makes the anticipated trajectory calculation more accurate. In this manner, the anticipated trajectory is calculated using the most up-to-date and accurate data points available, thus correcting for any drift or other error in the anticipated trajectory.

An exemplary tracking device that orients the recording device according to a trending movement of the target device will now be described with reference to FIG. 4.

As discussed herein, it is generally desirable to record the subject associated with the target device so as to produce a satisfactory recording. Where the target device undergoes rapid and/or erratic position changes, orienting the recording device according to the erratic movement of the target device may result in an unsatisfactory recording. In the case of a video recording of, for example, a mogul run skier holding the target device in their pants pocket, the target device would move rapidly up/down as the skier progressed along the mogul run and the resulting video recording would be likewise erratic if the recording device is oriented according to the strict movement of the target device. In such circumstances, the tracking device may function to orient the recording device according to the trending movement of the target device.

Figure 4:
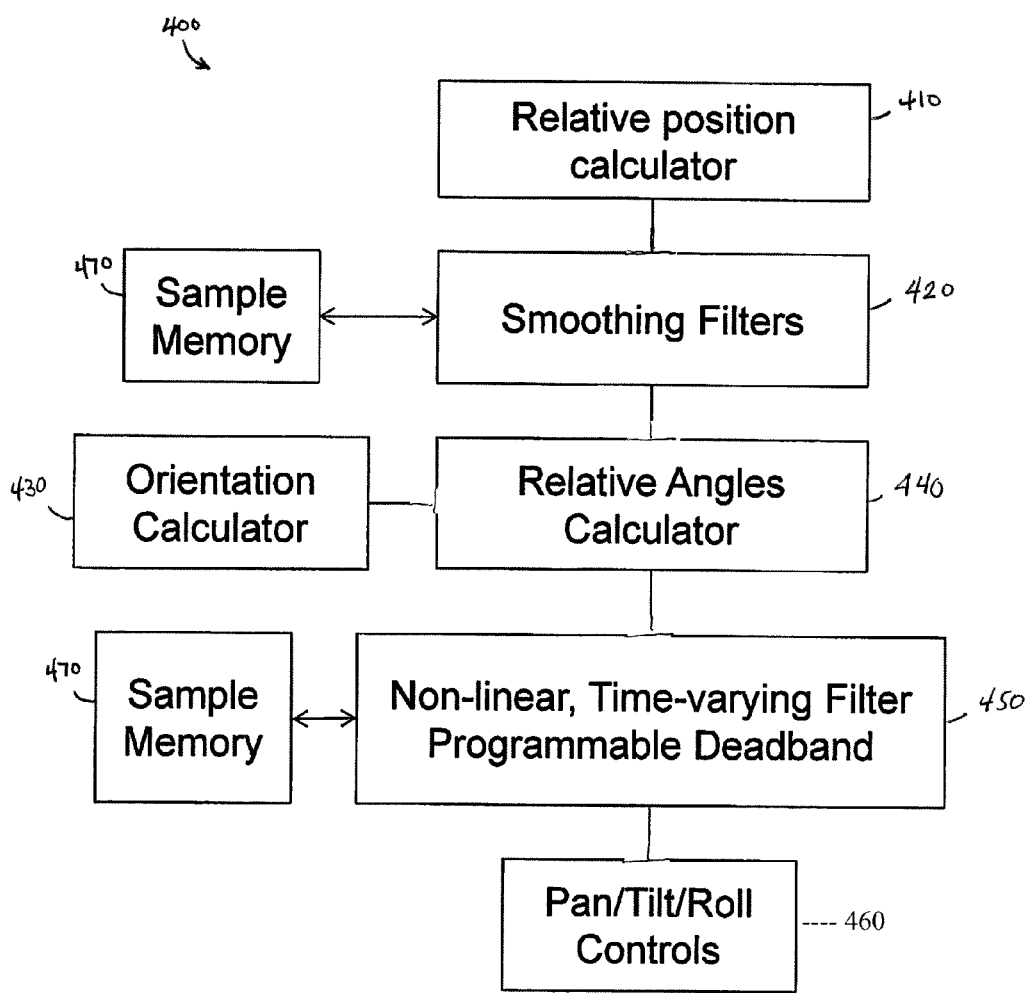
FIG. 4 schematically illustrates an exemplary tracking device that orients the recording device according to a trending movement of the target device according to at least one embodiment of the present invention.

As illustrated in FIG. 4, the tracking device 400 according to at least one embodiment further comprises a relative position calculator 410 for calculating the relative position of the target device (i.e., the position and trajectory vectors and/or the anticipated trajectory); a first smoothing filter module 420 communicatively coupled to the relative position calculator for applying a first smoothing filter to the relative position to generate the trending movement, the first smoothing filter being retrievably stored in a memory 470 communicatively coupled to the smoothing filter; an orientation calculator 430 for calculating the orientation of the recording device; a relative angle calculator 440 communicatively coupled to the orientation calculator and the smoothing filter for calculating adjustments to the recording device orientation based on the recording device orientation and the trending movement; and a second smoothing filter module 450 communicatively coupled to the relative angle orientation calculator for applying one or more a second smoothing filter to the calculated orientation adjustments, the second smoothing filter being retrievably stored in the memory 470 communicatively coupled to the second smoothing filter. Various smoothing filters and/or algorithms are known in the art and their application to data in the context of the embodiments described herein will be readily understood by one of ordinary skill in the art.

Exemplary smoothing filters preferably utilize one or more linear, non-linear and/or time-varying and/or dead band techniques to account for position interpolation and noise, as well as compensate for irregular movement.

Figure 5:
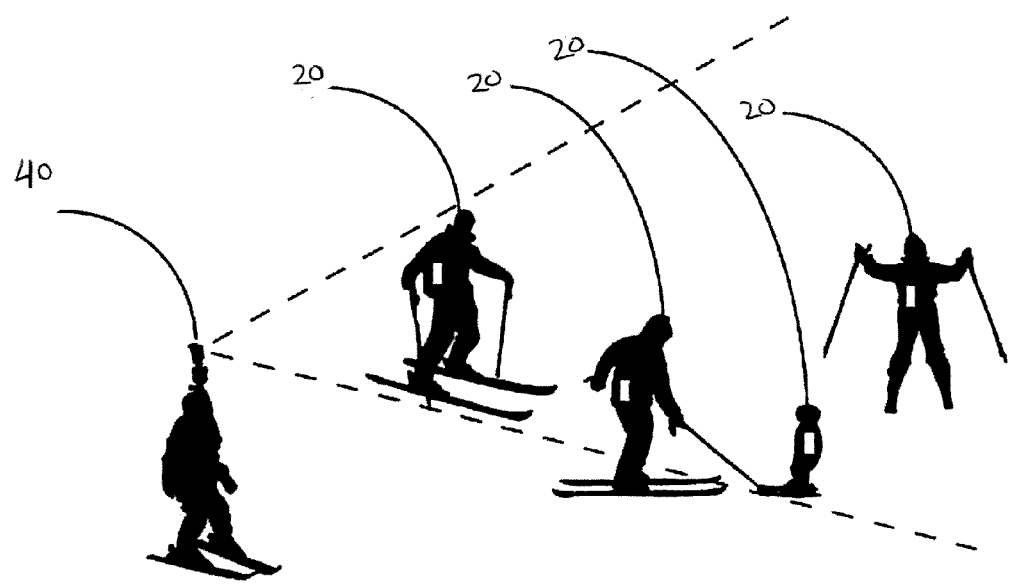
FIG. 5 schematically illustrates an exemplary recording system according to at least one embodiment of the present invention.

FIG. 5 schematically illustrates the recording system according to at least one embodiment of the present invention, comprising one or more target devices 20 communicatively coupled to one or more tracking devices 40 via the wireless network. It should be noted that the functionalities described herein with respect to single-device embodiments are likewise applicable to multi-device embodiments.

In some embodiments, a single tracking device may track multiple target devices. In such embodiments, each target device may be associated with a unique identifier transmitted to the tracking device in association with that target device's motion and/or position data. Recognition of each unique identifier is preferably preprogrammed into the tracking device—preferably as a register stored in the memory.

The tracking device may thus utilize the unique identifier (as well as the motion and/or position data) to determine the position and trajectory vectors for each target device, and orient the coupled recording device accordingly. In this manner, the recording of multiple subjects may be accomplished.

The tracking of multiple target devices may occur sequentially. For example, competitors of a skiing competition may each have a registered unique identifier. As each competitor singularly skis the competition run—or a desired portion thereof—the tracking device may track that competitor and orient the recording device accordingly. In this manner, sequential recording of multiple subjects may be accomplished.

The tracking of multiple target devices may occur simultaneously. For example, a group of snowboarders on a run together may each have a registered unique identifier. As the group of snowboarders proceeds down the run—or a desired portion thereof—the tracking device may track each snowboarder and orient the recording device accordingly. In some embodiments, the recording device will be oriented to retain all of the tracked subjects (e.g., snowboarders) within the recording range. In some embodiments, the recording device will be oriented to retain a subset of the tracked subjects—preferably a majority—within the recording range. In this manner, simultaneous recording of multiple subjects may be accomplished.

The tracking of multiple target devices may occur according to the unique identifiers of each target device. For example in the simultaneous tracking context, the tracking device may be programmed with one or more preferences given to select unique identifiers such that maintaining the associated subjects within the recording range is preferred to maintaining other subjects within the recording range. This preference may further be according to preprogrammed circumstantial logic. As a non-limiting illustrative example of circumstantial logic employed, the tracking device may be programmed to ensure recording of subjects B and C, but not to the detriment of recording subject A unless subject A is stationary. Further, in another example, in the sequential tracking context, the tracking device may be programmed to maintain each tracking device within the recording range for a predetermined period of time before switching to another tracking device, according to the unique identifiers. In this manner, recording multiple subjects according to the unique identifiers of their target devices may be accomplished.

The tracking of multiple target devices may also be weighted according to the position of each target. For example, when tracking a plurality of skiers down a run, the recording range may be oriented such that the recording device records the nearest skier to the tracking device. In this manner, recording multiple subjects according to their relative position may be accomplished.

As another example, in the same situation, the recording range may be oriented such that the recording device records each skier at one or more geographic locations (e.g., a particularly tricky or exciting part of a run). In other words, as each target device approaches the geographic location, a preference for that target device's unique identifier may be implemented.

The geographic location may be a preprogrammed absolute position, such as, for example a longitude, latitude, and/or altitude. In such circumstances, geographic location data, such as GNSS data or the like, may be provided that indicates the relative positions of the target device, the tracking device, and the geographic location. The GNSS data along with the motion data and the position data (as discussed herein) may then be utilized by the tracking device to calculate the position and trajectory vectors of each device relative to the geographic location.

The geographic location may alternatively be determined by a reference sensor positioned at the geographic location. In such embodiments, the reference sensor includes a transceiver for sending a geographic location signal (i.e., a beacon or a target device configured to identify the geographic location position data) to the tracking device. The geographic location signal, along with the motion data and the position data (as discussed herein) may then be utilized by the tracking device to calculate the position and trajectory vectors of each device relative to the geographic location.

Exemplary processes for relative position determination are described herein with reference to the tracking and target devices and are similarly applicable to geographic location utilizing embodiments. Accordingly, position and trajectory vectors for the target and tracking devices relative to the geographic location may be calculated utilizing geographic location data. In this manner, recording multiple subjects according to their positions relative to the geographic location may be accomplished.

In some embodiments, multiple tracking devices may track a single target device. In the simplest form of this embodiment, each tracking device operates independently of each other tracking device. However, embodiments in which each tracking device functions in cooperation with each other tracking device are also specifically contemplated.

In at least one embodiment, the tracking devices function cooperatively to 'hand off' recording of the target device as the target device leaves the recording range of one tracking device and enters the recording range of another tracking device. Accordingly, the tracking devices may exchange position signals, motion data and recording range data that may be used to calculate their relative positions and/or recording ranges.

It will be readily understood that the features of the embodiments described herein may be applied in various combinations. For example, multiple tracking devices may track sequential groups of target devices with preferences towards certain geographic locations, as well as preferences for target devices within each group.

Furthermore, in at least one embodiment, the functionalities of the tracking device are selectively controlled by a user via a user interface device communicatively coupled to the tracking device. The user interface device preferably permits the user to selectively control, for example, one or more of the pan, tilt, roll, zoom, focus, and activation components of orienting the recording device. The user interface device may further permit the user to choose the geographic location, set circumstantial logic or target device preferences, or otherwise selectively control any of the tracking device functionalities described herein.

The user interface device may be a graphical user interface device or any other type of user interface device now known or later developed. Preferably, the user interface device is wirelessly coupled to the tracking device, although wired embodiments are contemplated. For example, the user interface device may be integral to the tracking device and/or the target device. The user interface device may further be a dedicated device, although non-dedicated devices may also be utilized. For example, the user interface device may comprise a smart phone running a software application whose execution provides the smart phone with the user interface device functionalities described herein.

The user interface device preferably comprises one or more of: a button, a touchscreen, a microphone, and a sensor, operable to receive user inputted commands; one or more displays (e.g., LED indicator lights, LCD or OLED screens, etc.) for viewing status, alerts, prompts or other visual indicia; a transceiver for communicating data to/from the devices; and a controller for controlling the set-up and operation of the devices according to the functionalities set forth herein.

An exemplary tracking device will now be described with particular reference to FIG. 6-9, which schematically illustrate orienting the recording device in accordance with the calculated position and trajectory vectors of the target device according to at least one embodiment of the present invention.

As discussed herein, the target device periodically (i.e., continuously or at regular or irregular intervals) transmits its motion data and position signal to the tracking device, which utilizes the position signal and motion data to calculate the position and trajectory vectors of the target device. The tracking device then utilizes the calculated position and trajectory vectors, as well as its recording range data, to orient the recording device by changing the azimuth (i.e., pan), the elevation (i.e., tilt), the horizon (i.e., roll), the distance (i.e., zoom), the focus, and/or activation (i.e. on/off) of the recording device, such that the target device is within the recording range of the recording device.

Figure 6:
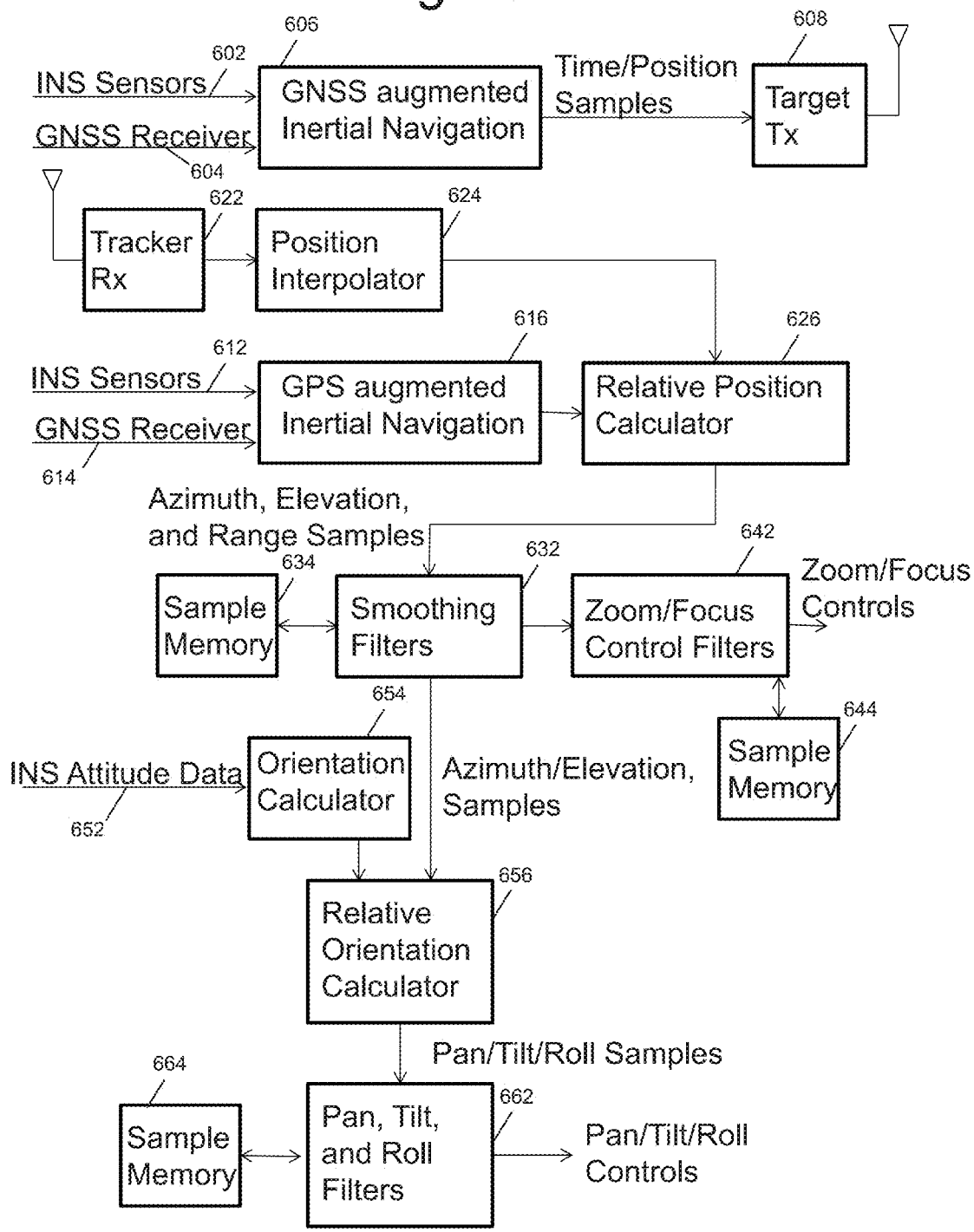
FIG. 6 schematically illustrates an exemplary process for orienting the recording device in accordance with the calculated position and trajectory vectors of the target device according to at least one embodiment of the present invention.

Turning to FIG. 6, INS motion data 602 is generated by the INS sensors of the target device. GNSS data 604 (or other objective positioning data) is generated by a GNSS receiver of the target device. The INS and GNNS data is communicated to an augmented inertial navigation module 606. The augmented inertial navigation module receives the INS and GNSS data, and calculates the position and/or trajectory vectors of the target device therefrom. In other words, the target device determines its trajectory from its INS and GNSS data. The target device trajectory (i.e., the position and trajectory vectors) is then communicated to the target device transceiver 608, which transmits the target device trajectory to the tracking device via a wireless network.

Figure 7:
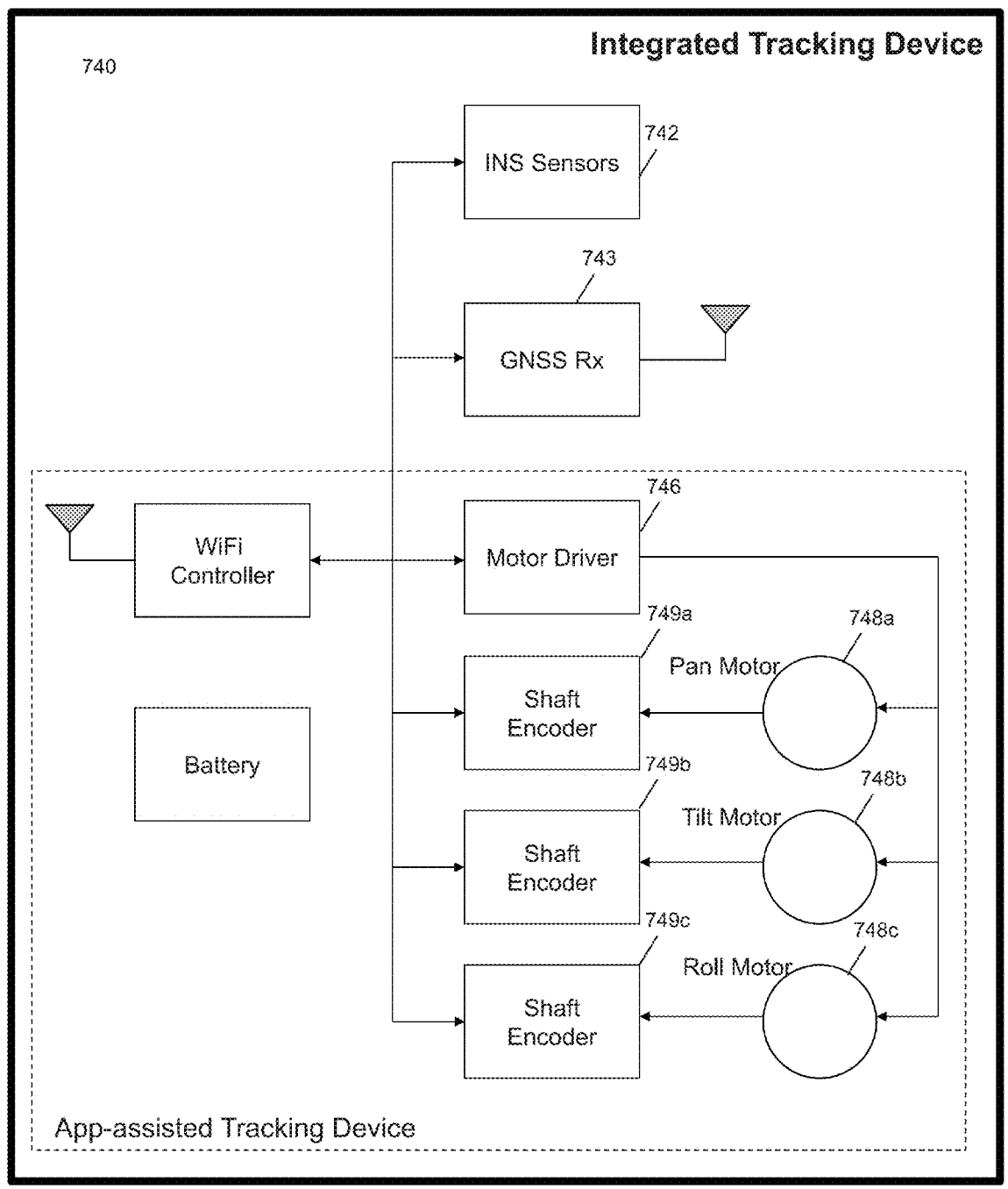
FIG. 7 schematically illustrates an exemplary tracking device according to at least one embodiment of the present invention.

Turning now to the tracking device, as reflected in FIGS. 6 and 7, INS data 612 for the tracking device 740 is generated by the INS sensors 742 of the tracking device. Tracking device GNSS data 614 (or other objective positioning data) is also generated by a GNSS receiver 743 (or the like) of the tracking device. The motion and GNNS data is communicated to an augmented inertial navigation module 616 of the tracking device (FIG. 6). The augmented inertial navigation module receives the motion and GNSS data, and calculates the position and/or trajectory vectors of the tracking device therefrom. In other words, the tracking device determines its trajectory from its sensor data.

As reflected in FIG. 6, the tracking device transceiver 622 receives the target device trajectory via the wireless network and communicates the target device trajectory to a position interpolation module 624, which generates an anticipated trajectory for the target device. In other words, the tracking device determines where the target device is going to be, as well as where it was between target data samples.

The anticipated trajectory for the target device and the trajectory of the tracking device are communicated to a relative position calculation module 626. The relative position calculation module utilizes both trajectories to generate a relative anticipated trajectory. In other words, the tracking device determines where the target device is going to be relative to the tracking device.

Staying with FIG. 6, a smoothing filter module 632 retrieves a stored smoothing function from memory 634, and applies the smoothing function to the relative anticipated trajectory to generate a trending anticipated trajectory.

Returning to FIG. 6, a zoom/focus filter 642 receives the trending anticipated trajectory from the smoothing filter module, as well as a zoom/focus function from memory 644. The zoom/focus filter applies the zoom/focus function to the trending anticipated trajectory to generate zoom/focus control data for controlling the zoom/focus orientation of the recording device. Preferably, control of the zoom/focus orientation of the recording device is such that the target device remains within the recording area. As described herein, adjustment of the zoom/focus orientation of the recording device may be accomplished via electrical and/or mechanical means in accordance with the zoom/focus control data.

Orientation data 652 provides the orientation of the recording device either directly, or as via utilizing parts of the tracking device as proxies, and generate orientation data therefrom. The orientation data is provided by orientation sensors that sense the orientation of one or more of the recording device, the tracking device and the mount. The orientation data is communicated to an orientation calculation module 654, which calculates the three-dimensional recording range of the recording device therefrom. In other words, the tracking device determines where the recording device is directed. For example, in the case of a video recorder, the calculated recording range may be a current field of view and sound for the video recorder.

The tracking device further comprises a relative orientation calculation module 656 communicatively coupled to the orientation calculation module and the smoothing filter module. The relative orientation calculation module receives the recording range and the trending anticipated trajectory and generates an adjusted orientation therefrom. The adjusted orientation reflects the orientation that the recording device should be in to satisfactorily record the target device according to its trending anticipated trajectory. In other words, the tracking device determines where to move the recording device so that the tracking device remains in the recording area.

A pan/tilt/roll filter 662 receives the adjusted orientation from the relative orientation calculation module, as well as a pan/tilt/roll function from memory 664. The pan/tilt/roll filter applies the pan/tilt/roll function to the adjusted orientation to generate pan/tilt/roll control data for controlling the pan/tilt/roll orientation of the recording device. Preferably, control of the pan/tilt/roll orientation of the recording device is such that the target device remains within the recording area. As described herein, adjustment of the pan/tilt/roll orientation of the recording device may be accomplished via electrical and/or mechanical means in accordance with the pan/tilt/roll control data.

Figure 8:
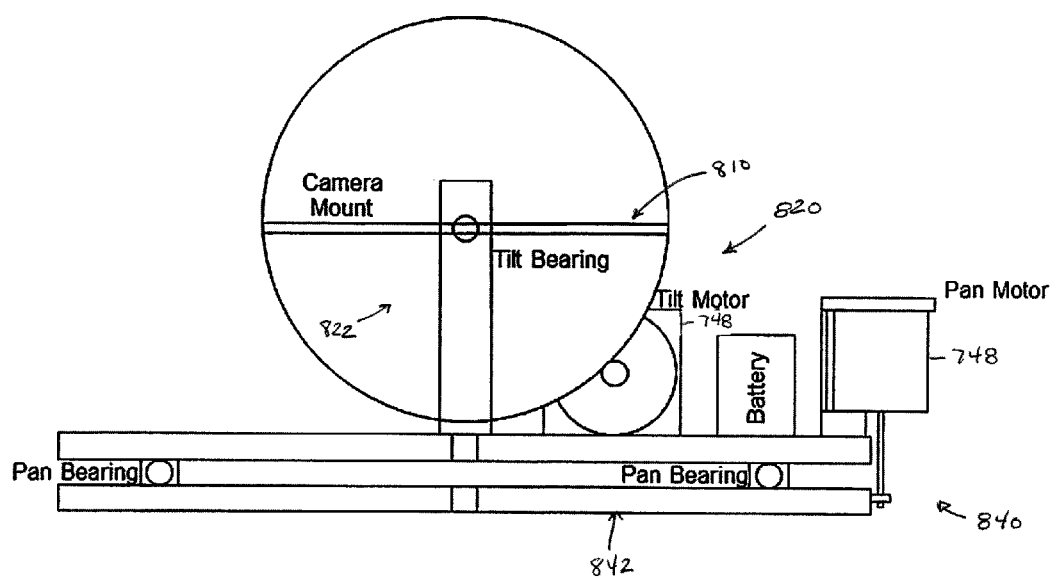
FIG. 8 schematically illustrates an exemplary means for controlling the pan, tilt and roll of the recording device orientation in accordance with at least one embodiment of the present invention.

Turning now to FIGS. 7 and 8, exemplary means for controlling the pan, tilt and roll of the recording device orientation in accordance with at least one embodiment of the present invention will now be described.

As reflected in FIG. 7, the tracking device is comprises: a pan motor 748*a* coupled to a pan shaft encoder 749*a*; a tilt motor 748*b* coupled to a tilt shaft encoder 749*b*; a roll motor 748*c* coupled to a roll shaft encoder 749*c*, each coupled to a motor driver 746. In operation, the motor driver and pan shaft encoder control the pan motor according to the pan control data in accordance with the principles of motor-shaft-encoder configurations. Similar functionalities exist for the tilt and roll motors and respective shaft encoders, which will be apparent to one of skill in the art. It will be appreciated by those of ordinary skill in the art that alternative actuators may be utilized, such as, for example, stepper motors with or without shaft encoders. Those of ordinary skill in the art will appreciate such variations are contemplated by the invention.

Turing to FIG. 8, the recording device is mounted on a mount 810 that is coupled to a tilt mechanism 820 comprising a tilt chassis 822 driven by the tilt motor for tilting the mount about a tilt axis, and a pan mechanism 840 comprising a pan chassis 842 driven by the pan motor for panning the mount about a pan axis perpendicular to the tilt axis. Such tilting and panning mechanisms are known to those of skill in the art. It will however be appreciated that other electrical and mechanical mechanisms for controlling the tilt/pan/roll orientation of the recording device may be implemented without departing from the scope of the invention.

In some embodiments, the tracking device is may be wearable, compact, lightweight, rugged, shock resistant, and/or have a low center of gravity. Preferably, the construction is with rigid, high strength materials, such as metals or hard plastics.

Figure 9:
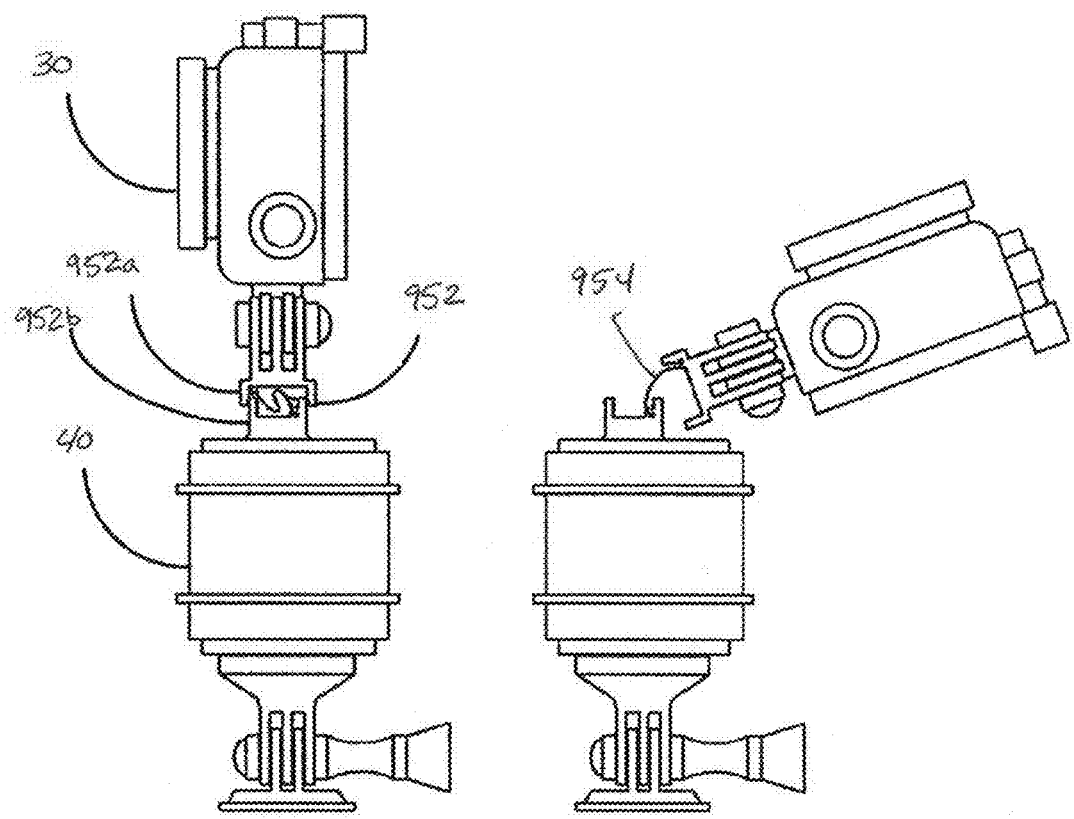
FIG. 9 illustrates an exemplary quick release in accordance with at least one embodiment of the present invention.

In order to minimize damage to the tracking device and/or recording device, one or more quick releases 952, as shown for example in FIG. 9, may be employed. The quick releases may be located at areas where there is a higher likelihood of damage in the event of an impact. The quick releases function as artificial breaking points for relieving impact stress that may otherwise damage the devices. In some embodiments, a tether 954 connects the halves (952a and 952b) of the quick release so as to retain the halves in close proximity when detached.

Turning now to FIG. 10, an exemplary user interface device will be described in which the functionalities of the tracking system are selectively controlled by the user.

The user interface is preferably a graphical user interface device, but may be any other type of user interface now known or later developed. Preferably, the user interface device is wirelessly coupled to the tracking device, target and/or recording device, although wired embodiments are contemplated. For example, the user interface device may be integral to the tracking device and/or the target device. The user interface device may further be a dedicated device, although non-dedicated devices may also be utilized. For example, the user interface device may comprise a smart phone running a software application whose execution provides the smart phone with the user interface device functionalities described herein.

A main screen 1000 is accessible to the user, having interactive controls (e.g., buttons, etc.) via which the user may access various control functionalities of the tracking system, including: target device control 1200, tracking device control 1400, recording device control 1600 and recording review/sharing control 1800.

The target device control screen preferably includes interactive controls via which the user may access and control one or more of the functionalities of the target device. The target device control screen may, for example, display the connectivity status 1220 amongst one or more of: the target device, the tracking device, the recording device, and the user interface device. The device control screen may also, for example, display an alert 1222 when one or more of the system devices is without (or with insufficient) connectivity.

A device calibration 1240 module for calibrating the tracking and target devices, i.e., for determining their relative positions from which the tracking functionalities described herein are accomplished, is accessible by the user via the target device control. Interfacing with to the device calibration may be via a device calibration screen, which may display device calibration information. The device calibration module may comprise various sub-modules, accessible via the device calibration screen, including one or more of: a device pairing module 1242 operable to permit the user to select the devices that will take part in the tracking (i.e., to pair one or more target devices with one or more tracking devices); a motion alert module 1244 operable to display a motion alert notifying the user when one or more devices are moving too much for an accurate calibration; a signal strength module 1246 operable to determine and display the strength of the signal transmitting the motion data and/or the strength of the position signal; and a status module 1248 operable to display the status of the calibration process.

Calibrating the tracking and target devices includes determining their initial relative positions and/or orientations, as described herein with reference to the tracking and target devices. Accordingly, the device calibration module (and screen) permits the user to initiate the calibration process. An exemplary process is briefly represented in the continuance of the flowchart of FIG. 10A at initial position module 1260 for illustrative purposes.

Inertial, positional and/or orientation data is provided by the inertial 1262, positional 1264 and/or orientation 1264 sensors. If no signal transmitting such data is received, an alert 1268 is displayed to inform the user of the error. The inertial and/or positional data is utilized to calculate the relative positions and/or orientations of amongst the devices via a location calculation module 1270, or the like, which preferably includes one or more of: an inertial calculation 1270-1 and a position calculation 1270-2. The calculated relative position/orientation is then transmitted to the user interface device via the relevant transceiver 1272. If the calibration is unsuccessful, the process is redone until successful (step 1274), at which point the calibration process is stopped (step 1276) and the successful calibration is reported via the status module.

The tracking device control 1400, including a tracking device control screen, includes interactive controls via which the user may access and control one or more of the functionalities of the tracking device. Such controls comprise one or more of: an on/off control 1420, and an actuator control 1440, including controls for pan 1442-1, tilt 1442-2 and roll 1442-3 actuators for manual tracking and/or calibration. Other tracking device functionalities described herein may further be controlled via the tracking device control.

Figure 10B:
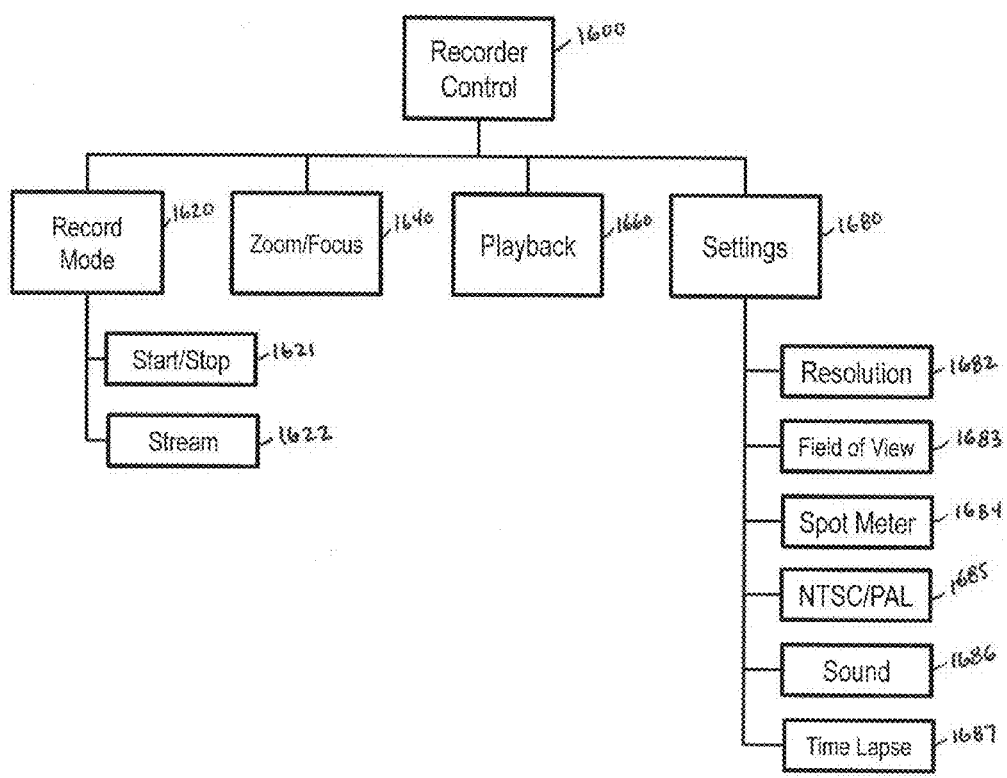

The recording device control 1600, including a recording device control screen, includes interactive controls via which the user may access and control one or more of the functionalities of the recording device. As illustrated in FIG. 10B, the recording device control may comprise various sub-control modules, accessible via the recording device control screen and including one or more of: a recording mode control 1620, including a start/stop/stand-by control 1621 and/or an online streaming control 1622; a zoom/focus control 1640 for controlling the zoom and/or focus of the recording device (to the extent applicable, e.g., for a video recorder); a playback control 1660, for initiating and otherwise controlling the playback display of one or more recordings; and a settings control 1680, for controlling the settings of the recording device, such settings for example in the video recorder context preferably including one or more of: resolution 1682, field of view 1683, spot meter 1684, NTSC/PAL 1685, sound 1686, and time lapse 1687. In some embodiments, one or more of the aforementioned controls may be implemented by interactive controls overlaid onto the display of a recording during playback. Other recording device functionalities described herein may further be controlled via the recording device control.

Returning to FIG. 10A, the recording review/sharing control 1800, including a recording review/sharing control screen, includes interactive controls via which the user may access and control one or more of the functionalities related to reviewing and/or sharing one or more recordings. These functionalities include one or more of: displaying selectable icons of recordings 1820; displaying playbacks of recordings 1840; displaying data related to the recordings (e.g., time, location, speed, map movement, distance, and/or other metric data recorded in association with the recording) 1860; transmitting 1880 selected recordings to an online server to be accessed by others (e.g., via social media, email, etc.). Other recording review/sharing control functionalities described herein may further be controlled via the recording review/sharing control.

Figure 11:
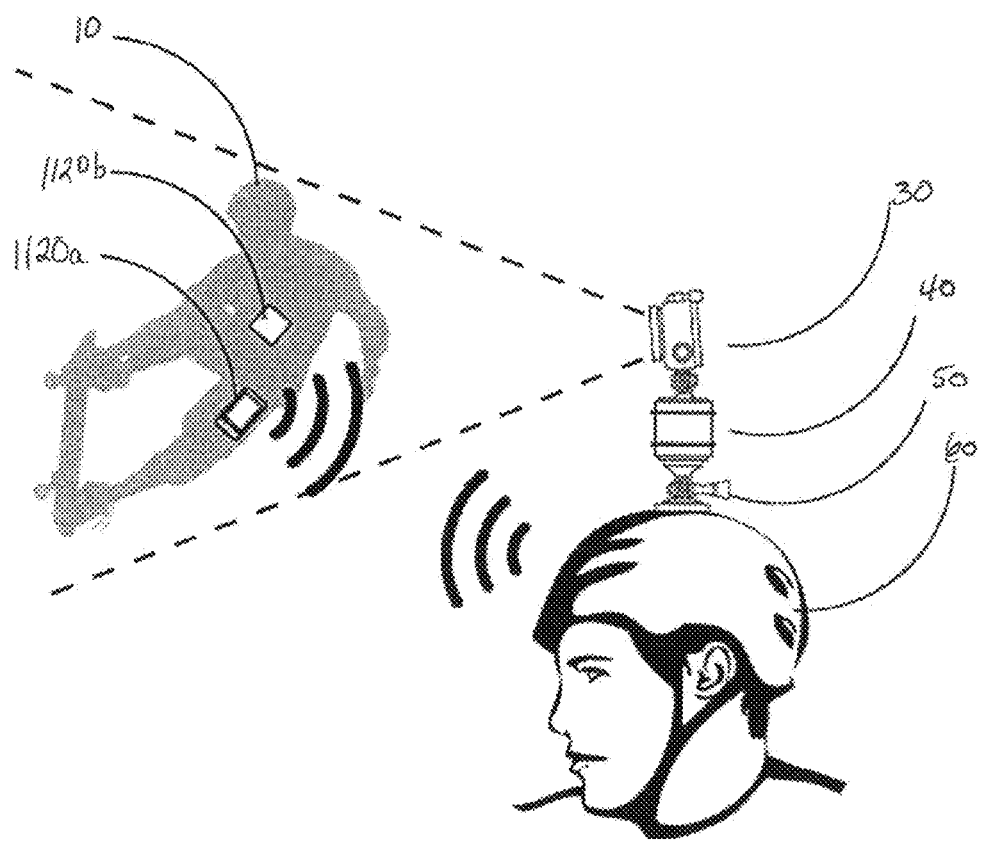
FIG. 11 schematically illustrates an exemplary recording system according to at least one embodiment of the present invention.

As illustrated for example in FIG. 11, in some embodiments, the target device may be a dedicated device 1120b communicatively coupled to a non-dedicated intermediary device 1120a, such as a smart phone (or other smart device, e.g., smart watch, smart glasses, etc.) running a software application that imparts the functionalities of the target device to the smart phone. The dedicated device may, for example, sense motion and position data and transmit that data to the non-dedicated intermediary device, which it turn transmits that data to the tracking device. The non-dedicated intermediary device may also comprise a user interface for one or more of the target device and the tracking device, through which the user may control the various functionalities of the target device and/or tracking device.

Figure 12:
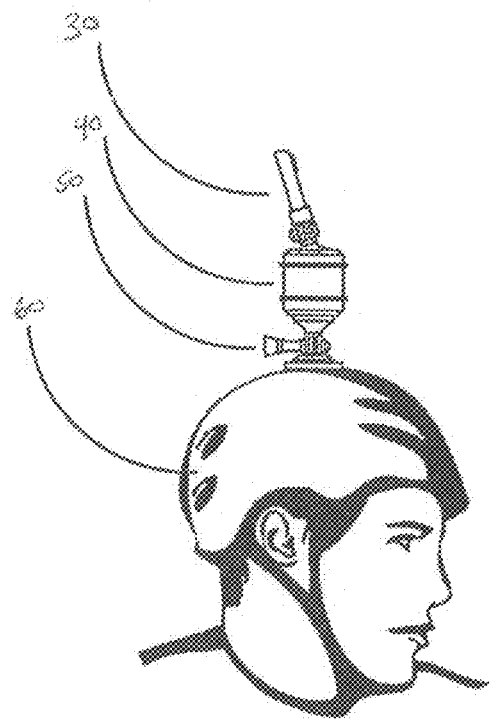
FIG. 12 schematically illustrates an exemplary recording system according to at least one embodiment of the present invention.

As illustrated for example in FIG. 12, in some embodiments, the recording device is smart phone camera running a software application that communicatively couples the smart phone to the tracking device such that the functionalities described herein are enabled. For example, zoom and/or focus features of the smart phone camera may be implemented via wireless coupling with the tracking device such that zoom and/or focus signals from the tracking device are received by the smart phone and thereby cause the smart phone camera to zoom and/or focus accordingly.

In some embodiments, the tracking device comprises a smart phone running a software application that imparts the tracking device functionalities described herein to the smart phone. In such an embodiment, the smart phone may be communicatively coupled to the electro-mechanical means for orienting the recording device so as to control the orientation of the recording device in accordance with the functionalities described herein.

Figure 13:
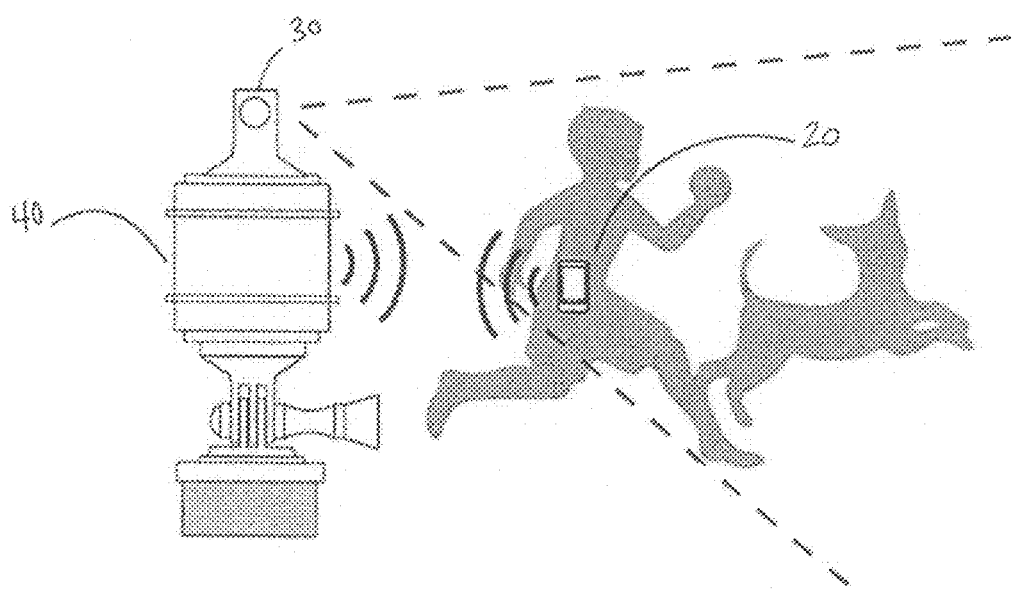
FIG. 13 schematically illustrates an exemplary recording system according to at least one embodiment of the present invention.

As illustrated for example in FIG. 13, in some embodiments, the tracking device and recording device comprise an integrated piece.

Further embodiments will now be described with reference to the figures.

In at least one embodiment, the mobile, wearable, automated target tracking system consists of one or more target devices (smart phone, other app-based smart device—watch, eyeglasses, etc., or a dedicated wearable target device), video or still cameras and/or recording devices (most likely small, lightweight POV cameras or smart phone cameras), tracking devices and wearable mounts or tripods. See, for example, FIG. 1. The system is designed to function independent of the video or camera device and/or the mounting system. An alternative method would allow the system to be integrated with a camera device.

The automated system allows a person carrying or wearing the target device to be tracked while in motion so as to be visible in the video or still image frame of the camera device recording. The target device communicates its position with an appropriate frequency to the tracking device which also knows its position and orientation relative to the target device. A camera or other image and/or sound capture device may be mounted to the tracking device. The tracking device may be in motion either attached to a moving person, boat, motorcycle, car or other object. Therefore the tracking device calculates the relative position of the target device compared to its own position and changes its azimuth (pan), elevation (tilt) and/or horizon (roll) in order to maintain the target within the field of view or frame of the recording device. In applications that require tracking along two axes of motion, the system will allow for operation of pan and tilt only.

The tracking device is a compact, portable, lightweight, ruggedized electromechanical device, which determines where the target device is located relative to itself based on the relative position of the target device to the tracking device and its orientation, the tracking device will pan, tilt and/or roll to point at or near the target device. As available, the tracking device can also control focus and zoom, given that the target range is also measured.

The method utilized to track the target is designed to be used in either an outdoor or indoor environment. Both the target device and the tracking device may be moving in a quick and unpredictable manner. Therefore the tracking technique must be able to monitor very fast changes in the position of the target device and the tracking device. Although a GNSS can be used to determine absolute location of a person or object, GPS may not provide location information at a high enough frequency to track the position of a target device that may be moving quickly or rapidly. GNSSs also do not provide orientation information and cannot be reliably used in all indoor and some outdoor environments.

A tracking method used is based on INS sensors. See, for example, FIG. 2. The target device utilizes accelerometer, gyroscopic, magnetic, and/or barometric sensors (and optionally augmented by GPS) to determine its own motion. From acceleration data, the target device can determine its velocity and distance traveled in three dimensions. The tracking device also utilizes an accelerometer, gyroscopic, magnetic, and/or barometric sensors (and optionally augmented by GPS) to determine its movement and orientation. The target device communicates its position and movement information via an RF signal either directly or indirectly to the tracking device. The tracking device calculates the relative position, direction vector and range, of the target device to itself utilizing the position and movement information provided by the target device and its own movement data. The tracking device will use the relative target position calculation and its own orientation data to determine where to point to maintain visibility of the target device. The tracking device may also use the range calculation to control the camera zoom and focus.

Inertial navigation requires that the target device and the tracking device calibrate their initial relative position. The target device UI will prompt the target to initialize the system before the start of the tracking sequence. The target device and the tracking device will communicate and initialize the system. At this point, as available, GPS will be used to locate both the target device and the tracking device and create a reference point for the start of the inertial navigation sequence.

Over time, the inertial navigation technique will begin to introduce drift and some error in the relative positioning tracking system. In order to minimize drift, GNSS may be used to reset the relative positions of the tracking device and the tracking device. GNS, as available, may be used as often as target and tracking device motion profile demands in order to minimize drift. See, for example, FIG. 3.

The tracking device will change its azimuth (pan), elevation (tilt) and horizon (roll) in conjunction with the movement of the target device. However, the main objective of the tracking device is to follow the target, not the target device and to keep the target in the field of view or frame of image or video. Therefore the tracking device should only pan or tilt if the target is moving significantly outside the center of the frame. In some cases it is possible that the target device is moving rapidly back and forth or up and down but the target is moving much more slowly than the target device. An example would be a skier on a mogul run with the target device located in their pants pocket. The target device is moving rapidly up and down, but the target is moving smoothly down the hill. In this case the tracking device should not move up and down rapidly to follow the strict movement of the target device but should follow the trending movement of the target device. Additionally, the target device (and target) may accelerate or decelerate very quickly, as in the case of a motorcycle, or the target device (and target) may change direction very suddenly, as in the case of a skateboarder. In these scenarios the tracking device should not jerk too quickly to follow the target, but its motion should be smoothed out over time to provide a more pleasing image recording even if it allows the target to move outside of the center of the image frame. Smoothing algorithms, utilizing various linear, non-linear and/or time-varying filtering techniques as well as programmable deadband methodologies, will be used to account for position interpolation and noise, as well as compensation for irregular movement as in the case of the mogul skier and the motorcycle and skateboarder. See, for example, FIG. 4.

The target device may be tracked at a very short range from the tracking device up to a very long range. Under normal tracking conditions, the target device will be no more than a couple hundred feet from the tracking device. Under these circumstances the target device will connect directly to the tracking device via RF communications. This connection can utilize the unlicensed RF spectrum that exists in several frequency bands.

If the target device is a dedicated, wearable device, the communication range may be much longer than a couple hundred feet and will be determined by transmit power of the target device and the antenna gain of the tracking device. A target device can be a smart(phone) device. In this case if very long range tracking will be required, the preferred communication method will be to establish an internet connection between the target device and the tracking device. The smart target device will connect to the internet and a dedicated server device will route the target data to the tracking device over the network. If a dedicated server device is not available the preferred method would be for the target device to establish a voice circuit connection to the tracking device. Data would be transferred from the target device to the tracking device via standard telephone modem protocols.

Tracking of one target device by one tracking device will be the most common use case: Other use cases are: (1) track multiple target devices from one tracking device, (2) track one target device from multiple tracking devices and (3) track multiple target devices from multiple tracking devices. See, for example, FIG. 5.

In case (1), the tracking device may sequentially track multiple target devices. For example in a ski race course, multiple skiers wearing target devices will be tracked by the tracking device at different times. Each smart target device from each skier will register and establish a unique ID code with the tracking device via the UI of the device and a direct RF connection with the tracking device. The tracking device will listen for all target device electronic IDs. The target device will initiate a start button to transmit their unique ID code. Each new start will signal the tracking device to track the next unique ID code.

In case (1) the tracking device may track multiple target devices simultaneously. For example, four snow boarders may be taking a run together. The tracking device, which is mounted on one of the snow boarders' helmets, may be programmed via one of the target devices over RF communication to track all target devices in the same frame. If all target devices cannot be tracked together in the same frame there may be a priority order of tracking for the target devices. Or the tracking device may be programmed via the target device to track each target device for a specified period of time before switching to the next. Or the target device may manually switch the target device to be tracked via RF communication with the tracking device.

In case (2) multiple tracking devices may track one target device. For example, a mountain biker may traverse a trail in which multiple tracking devices are set up at different locations along the trail. The target device can communicate via RF to all tracking devices and register as a tracking device. When the biker gets in range of each tracking device, it will be tracked throughout each tracking devices' range.

In case (3) multiple target devices may be tracked by multiple tracking devices. For example, in surveillance scenario, multiple security guards maybe tracked by multiple tracking devices as the guards monitor a large venue such as a concert or sporting event. The tracking devices maybe programmed directly to track all security guard target devices. Or the target devices may manually control when and how they are tracked by each individual tracking device or all tracking devices.

The tracking device is a portable, ruggedized electromechanical device. The tracking device is designed to be wearable and mobile and therefore must be lightweight, compact and battery operated. The tracking device may include two or three motors to control pan and tilt or pan, tilt and roll of the camera and/or image and sound recording device that is mounted to the tracking device head. It may also include electronics to run operating software which will ultimately control the motors. The tracking device may be integrated at different levels. The most basic would only include only the motors and controllers and would be controlled externally by another device such as a smart phone. At the next level of integration it may include the motors, controllers and electronics, sensors and software to track and control its movement. At the highest level of integration, the tracking device may also include a fully integrated camera device in order to control camera functions in coordination with camera movement.

The tracking device will be capable to receive the target device position information on a periodic basis. The tracking device will also be capable to determine its movement, position and orientation on a periodic basis and calculate the relative change in position of the target device. Based on the updated target device position and the current angle of the tracking device head, the pan, tilt and roll motors will be adjusted to change the angle of the tracking device head to point at or near the target device. If the target device has not moved a significant distance and the tracking device has not changed position and orientation, the pan and tilt angles will not be adjusted. The tracking device will utilize the smoothing algorithms to regulate the control of the tracking device head movement. See, for example, FIG. 6.

The Tracking device may be implemented in an integrated fashion which would require it to include all electronics for connecting with the target device (RF), exchanging data, sensing position and orientation, calculating relative position and necessary angle of tracking device head as well as execution of the smoothing algorithms. The tracking device may also be executed as an App-assisted device. In this scenario, a smart phone (or other appropriate device) would be utilized to perform most of the complex operations including connection to the target device, sensing of position and orientation, calculation of relative position/angle and execution of the smoothing algorithms. See, for example, FIG. 7.

The integrated tracking device implementation may be based on an embedded hardware/software platform. The embedded solution would allow for a very high performance, real time system and would not require the use of a smart phone or other device for tracking.

The basic hardware configuration for an integrated tracking device may include a controller, memory, I/O, GPS, accelerometer and orientation sensors and RF transmit and receive capability (i.e. WiFi, Bluetooth). The operating system shall support the hardware features mentioned above. The integrated tracking device operating software will execute all of the tracking functions including connecting and communicating with the target device, calculating relative position, correcting drift, smoothing target device motion, controlling the drive movement of the pan, tilt and roll motors and managing the user interface. The integrated tracking device user interface may be executed in one or more of the following; segmented LCD or full active touch screen together with hard or soft buttons and LED indicator lights.

The App-assisted tracking device would be based on a smartphone platform which provides for easy and quick software development, a high level of functionality, extensibility and capability for simple software updates. It also would eliminate the cost of the bulk of the electronics included in the integrated tracker device. It would require the user to use a smart phone device with custom app to fully operate the App-assisted tracking device. The smart phone would require a GNSS receiver and INS sensors, and an RF network I/F (i.e. WiFi, Bluetooth). The smart phone would calculate the necessary angle change of the tracking device head and communicate that to the App-assisted tracking device either wirelessly or wired.

In the case where the App-assisted tracking device is stationary, the target device smart phone would be able to function as the App-assisted smart phone as well. By initially calibrating the target device smart phone next to the stationary App-assisted tracking device, the target device smart phone would record the exact position of the tracking device. The target device can use the tracking device position to determine the differential movement of the target relative to the stationary tracking device. If the App-assisted tracking device is moving during the tracking process, then a second smart phone would be required to determine position/movement and orientation of the App-assisted tracking device.

The tracking device may also include a camera/image recording device control interface for intelligent control of zoom and focus or other imaging or sound related features on the recording device. Using the range calculations, the tracking device may control the zoom and focus of the camera or recording device in a way that maintains the visibility and framing of the target at different ranges throughout recording. The tracking device could control other camera functions such as aperture or gamma based on a pre-programmed schedule or manual control from a target device (or via a light level sensor).

The tracking device may contain three motors for pan, tilt and roll. All motors would be capable of 360 degree rotation. The panning function requires implementation of a full 360 degree rotation with the ability of the tracking device to continuously pan to more than 360 degrees in an unlimited fashion. The tilt function of the tracking device may only be implemented to rotate 180 degrees. The roll motor rotation may also be limited based on the width and height of the camera device attached to it. See, for example, FIG. 8. An example of how control of the roll third axis may be implemented is to maintain frame leveling with the horizon. If roll is experienced by a person, or vehicle or other object that the tracking device is mounted to, then the image frame may not line up with the horizon. An example would be a tracking device mounted to the handlebars on a mountain bike. As the rider leans into a turn, the roll angle will be changed and the horizon may no longer be square to the image frame. A third motor would be able to compensate for this change in roll angle.

The tracking device motors may be stepper motors or continuous motors/servos, or position servos that would not require shaft encoders. Stepper motors offer low cost, high reliability, high torque at low speeds and a simple, rugged construction that operates in almost any environment. Stepper motors do not inherently provide a closed loop feedback system. Continuous servo motors with shaft encoders for pan, tilt and roll would likely be utilized for higher performance product designs.

Pan, tilt and roll mechanisms will require driver circuits to supply the necessary current and voltage to drive the motors. In addition, a controller device will be required to interface from the smartphone or embedded system to the motor drivers. Since the system is designed to be mobile and wearable, the cameras and recording devices to be attached to the tracking device will be low in mass. Therefore the motors will have appropriate torque requirements and will be able to accelerate and decelerate quickly and smoothly.

The tracking device will be wearable and therefore will be constructed to be compact and lightweight with a low center of gravity. Since the tracking device will be mobile and will be used in action sports, motor sports and other high speed activities, the construction will be rugged and the device will be shock resistant. The tracking device may be subject to significant G-force and therefore will be designed with high strength materials and rigid construction. The camera or recording device that is attached to the tracking device may also be subject to high G-force impact which could compromise the integrity of the tilt/roll mechanisms. In order to minimize the stress to the mechanisms during impact, the tracking device or a tracking device accessory will be constructed with a quick release connection that will detach if impact exceeds the allowable G-force. See, for example, FIG. 9.

The tracking device will be designed with the necessary sealed construction to maintain water resistance. The mechanics and electronics will be designed to provide high performance operation with minimum power consumption. The tracking device will be rechargeable and offer removable battery capability. Since the integrated tracking system will be used outside in most cases, a solar battery charger may be built in or provided as a custom accessory.

The integrated tracking device may be used in the upward facing position or the downward facing position. The pan, tilt and roll mechanism as well as the tracking system will be designed to enable both upward and downward operation. The App-based tracking system will either auto-sense the orientation of mounting or be designed to enable the user to select upward or downward mode via the touchscreen interface of the smart phone or smart device.

The target device may be a smart phone or other smart, app-based device or it may be a dedicated wireless RF transceiver device or it may be a combination of both smart phone and dedicated wireless transceiver device. One scenario is that the target device is a smart phone or other general purpose smart device that runs a specific target app. See, for example, FIG. 10. The target device app will essentially utilize the capabilities of the smart phone such as sensors and GPS locator to determine position data for the target device. The app will tap the smart phone RF transceiver capability to transmit position data and other vital information to the tracking device for relative positioning calculations.

Utilizing a general purpose, app-based, smart phone or smart device as a target device rather than a dedicated device has many advantages for the user. The smart phone offers a rich user interface which can include touch, voice, and/or gesture control. The smart phone provides a familiar and comfortable interface for the user. It also provides a platform to run other applications in addition to the automated, target tracking app. For example, if an app-compatible camera is mounted to the tracking device, the target device may be able to view streaming video directly from the camera in real time or time shifted video. The smart phone also offers almost unlimited versatility in accessories and apps. Hundreds if not thousands of different wearable accessories, ruggedized and waterproof cases and additional accessories and apps are available.

In more specialized use cases or extreme environments where heavy vibration or gravitation forces are present or where extreme accuracy is desired, the target device may be a hybrid smart phone and dedicated sensor device. The sensor device may be capable of receiving GPS data as well as measuring accelerometer and other sensor data. This data would be transferred to the smart phone device. The smart phone would also provide a robust UI to set up and control the sensor device. See, for example, FIG. 11.

The basic functional requirements of the target device are GPS navigation, motion sensors and RF communications capability. Additional sensors may be included such as impact, orientation or even bio monitoring.

The target device may also be used as a remote control for the tracking device. The target device can control pan, tilt and roll via RF communication between the target device and the tracking device. The smartphone provides for a robust UI and a convenient form factor. See, for example, FIG. 12. For example, a parent who is recording video of their child in a school play or activity could set the tracking device with a mounted video camera on a tripod near the stage. They could then sit in the audience and control the tracking device (and camera) remotely. The target device would connect to the tracking device via RF and the app on the target device (smart phone) would provide the UI for real-time control of the camera pan and tilt.

Many smart phones now provide multi-tasking capabilities. In addition, many cameras and video recording devices are being packaged with smart phone apps that allow them to be controlled remotely and provide for streaming video to a smart phone or tablet. The target device, when used in conjunction with a camera streaming app, could utilize visual feedback in order to manually adjust the tracking device to keep a subject or object in frame. Before, during or after tracking, the target device might use the video streaming to monitor how well the target is being captured in the video frame of the camera and make adjustments or recalibrate with the tracking device if necessary. The target may also start, stop, zoom, focus or control the camera remotely while being tracked in order to provide the best possible video recording. See, for example, FIG. 13. Using a smart phone or smart device as the target device, provides a universal platform for apps to be utilized in conjunction with the target app which will expand the functionality of the universal, wearable, automated, target tracking system.

In addition to the universal, wearable, automated, target tracking system, the tracking device may be used in a more specific smart phone camera target tracking system. See FIG. 12, Smart Phone Camera Target Tracking System Configuration. Smart phone camera capability continues to improve and they are being used more and more as the main image recording device for many consumers. In this system application, the smart phone acts as the camera or image recording device and is mounted on the tracking device. The smart phone may also be used in conjunction with an App-assisted tracking device and will act as the brains for the target tracking system while at the same time provide the image recording capability for the system.

In the smart phone camera target tracking system, the target app can be combined with the camera control features and from one interface the target app can control start, stop, zoom, focus, video streaming and other camera functions while at the same time provide the control and UI for the tracking system. The combined app will also enable automated target tracking coordinated with camera control. This will enable auto zoom and focus while tracking and automated aperture, frame and motion stabilization control during tracking as well.

A second, more specific target tracking system may be deployed. The all-in-one camera target tracking system provides a convenient form factor for the wearable, automated target tracking system. See, for example, FIG. 13. The All-in-One system combines a full function still and video camera with the tracking device in one easy-to-use package. The advantage of the All-in-One is fully integrated functionality between the camera and the tracking device. It would provide all the features of the smart phone camera target tracking system with even greater performance and capabilities. The tightly coupled interaction of camera and tracking system would enable automated or manual control of all camera and tracking simultaneously. The system would also benefit from a more efficient mechanical construction and therefore reduced size, weight and footprint.

In some embodiments, the system will capture object position data and/or other sensor data and may record separately as data for later viewing of historical positioning and/or sensor conditions. Or the position/sensor data may be time code linked to the associate video in order to provide a complete view of the object movement and condition.

Although the global navigation satellite system GNSS, (can be used to determine absolute location of a person or object, GNSS may not provide location information at a high enough frequency to track the position of a target device that may be moving quickly or rapidly. In order to increase the accuracy of GNSS, the target may utilize GNSS together with satellite, SBAS, and ground, GBAS, based augmentation systems such as WAAS, LAAS, EGNOS, GAGAN and MSAS, as well as proprietary schemes to improve the real time accuracy of the GNSS.

In some embodiments, tracking is based on sensors. The target device may utilizes a GNSS and/or an inertial navigation system ("INS"). For example, 10 DOF sensors may be utilized, comprising: 3 accelerometers, 3 gyros, 3 magnetometers, and a barometer, to provide motion data for 3D inertial data processing. In this manner, the target device may determine its own motion. From such data, the target device can determine its velocity and distance traveled in three dimensions. The tracking device may also utilize GNSS and/or INS data to determine its movement.

In some embodiments, the target device and the tracking device may calibrate their initial relative position. The target device user interface may prompt the target device to initialize the system before the start of the tracking sequence. The target device and the tracking device may communicate to initialize the system. As available, GNSS may be used to locate both the target device and the tracking device and create reference points for the start of the INS sequence.

In some embodiments, the integrated tracking device may include a controller; a memory; an input/output interface; GNSS and/or INS sensors; and an RF wireless transceiver. Additional sensors may be included such as impact, orientation or bio monitoring sensors.

In some embodiments, the tracking device user interface may comprise the user's smart phone or other smart device such as smart watch, smart glasses, etc., communicatively coupled to the tracking device. The user interface may allow for the set-up, initialization, monitoring or control of the tracking device functionalities. The user interface may further allow accessing the recording (e.g., viewing of the recorded video) via a wireless stream from the tracking device.

In an example according to at least one embodiment, a child may wear the target device during a soccer game, while the tracking device and coupled camera are set up on a tripod near the field. The parent may sit in their seat off the field and monitor the wirelessly streamed video on their smart phone or tablet or other smart device. The parent may further modify the configuration of the automated tracking or manually control the tracking device and/or camera remotely to change pan or tilt camera or zoom, focus, start/stop recording on camera (i.e., to orient the camera).

In some embodiments, the tracking devices and/or recording devices may further be connected to a LAN or internet gateway to multicast recordings from one or more tracking systems which would allow local or remote viewing of live or time shifted video by multiple simultaneous users. The local or remote user could be granted access to control the tracking system or camera and to switch between tracking systems.

The enablements described in detail above are considered novel over the prior art of record and are considered critical to the operation of at least one aspect of the invention and to the achievement of the above-described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim. Further, the various features of the several embodiments described herein may be mixed-and-matched without departing from the scope of the invention.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

Furthermore, the functionalities described herein may be implemented via hardware, software, firmware or any combination thereof, unless expressly indicated otherwise. If implemented in software, the functionalities may be stored in a memory as one or more instructions on a computer readable medium, including any available media accessible by a computer that can be used to store desired program code in the form of instructions, data structures or the like. Thus, certain aspects may comprise a computer program product for performing the operations presented herein, such computer program product comprising a computer readable medium having instructions stored thereon, the instructions being executable by one or more processors to perform the operations described herein. It will be appreciated that software or instructions may also be transmitted over a transmission medium as is known in the art. Further, modules and/or other appropriate means for performing the operations described herein may be utilized in implementing the functionalities described herein.

The scope of this description is to be interpreted only in conjunction with the appended claims and it is made clear, here, that the named inventors believe that the claimed subject matter is what is intended to be patented.

What is claimed is:

1. A system for recording a subject, the system comprising:
 a target device proximal to the subject, the target device comprising:
  one or more target sensors sensing the position and/or motion of the target device and generating target trajectory data therefrom;
  a target transceiver communicatively coupled to the wireless network, the target transceiver transmitting the target trajectory data via the wireless network;
 a recording device having a recording range, the recording device displaced from the subject and recording the subject within the recording range; and
 a tracking device operatively coupled to the recording device, the tracking device comprising:

one or more tracking sensors sensing the position and/or motion of the tracking device and generating tracking trajectory data therefrom;

a tracking transceiver communicatively coupled to the wireless network, the tracking transceiver receiving the target trajectory data transmitted by the target device;

a recording range sensor for sensing the recording range of the recording device and generating recording range data therefrom;

an orienting apparatus for adjusting the recording range of the recording device based on the received target trajectory data, the generated tracking trajectory data, and the sensed recording range.

2. The system of claim 1, wherein the orienting apparatus generates an anticipated target trajectory based on the received target trajectory and the sensed tracking trajectory, and wherein the orienting apparatus adjusts the recording range based on the anticipated target and tracking device trajectories, and the recording range.

3. The system of claim 2, wherein the anticipated target trajectory is a relative trajectory between the tracking device and the target device.

4. The system of claim 1, wherein the tracking trajectory data includes position and motion data.

5. The system of claim 1, wherein the target trajectory data includes position and motion data.

6. The system of claim 1, wherein the tracking device and the recording device are positioned at a stationary location.

7. The system of claim 1, wherein the tracking device and the recording device are positioned at a non-stationary location.

8. The system of claim 1, wherein the recording range data includes data indicating the orientation of the recording device.

9. The system of claim 1, wherein the orienting apparatus comprises at least one of: a tilt mechanism for adjusting the tilt of the recording device, a pan mechanism for adjusting the pan of the recording device, and a roll mechanism for adjusting the roll of the recording device.

10. The system of claim 1, wherein the orienting apparatus adjusts the recording range by changing one or more of the following orientations of the recording device: tilt, pan, roll, zoom, focus, and activation.

11. The system of claim 1, wherein trajectory data includes stationary trajectory data.

12. The system of claim 1, wherein the wireless network is a radio-frequency network.

13. The system of claim 1, wherein the target device comprises a smart phone.

14. The system of claim 1, wherein the tracking device comprises a smart phone.

15. The system of claim 1, wherein the recording device comprises a smart phone.

16. The system of claim 1, further comprising a user interface device communicatively coupled to and operable to permit a user to interface with one or more of: the tracking device, the target device, and the recording device.

17. The system of claim 16, wherein the user interface device is a smart phone executing a computer application whose execution causes the smart phone to permit the user to interface with one or more of: the tracking device, the target device, and the recording device.

* * * * *